US010160652B2

(12) United States Patent
Galimberti et al.

(10) Patent No.: US 10,160,652 B2
(45) Date of Patent: Dec. 25, 2018

(54) ADDUCTS BETWEEN CARBON ALLOTROPES AND SERINOL DERIVATIVES

(71) Applicants: POLITECNICO DI MILANO, Milan (IT); PIRELLI TYRE S.P.A., Milan (IT)

(72) Inventors: Maurizio Stefano Galimberti, Milan (IT); Vincenzina Barbera, Biancavilla (IT); Roberto Sebastiano, Lazzate (IT); Antonio Marco Valerio, Sesto S. Giovanni (IT); Gabriella Leonardi, Milan (IT); Attilio Citterio, Milan (IT)

(73) Assignees: Politecnico Di Milano, Milano (IT); Pirelli Tyre S.p.A., Milano (IT)

( * ) Notice: Subject to any disclaimer, the term of this patent is extended or adjusted under 35 U.S.C. 154(b) by 0 days.

(21) Appl. No.: 15/514,350

(22) PCT Filed: Sep. 30, 2015

(86) PCT No.: PCT/EP2015/072641
§ 371 (c)(1),
(2) Date: Mar. 24, 2017

(87) PCT Pub. No.: WO2016/050887
PCT Pub. Date: Apr. 7, 2016

(65) Prior Publication Data
US 2017/0275169 A1 Sep. 28, 2017

(30) Foreign Application Priority Data
Oct. 1, 2014 (IT) .............................. MI2014A1714

(51) Int. Cl.
*C07D 207/33* (2006.01)
*C01B 32/152* (2017.01)
*C07D 207/333* (2006.01)
*C09C 1/56* (2006.01)
*C01B 32/174* (2017.01)
*C01B 32/20* (2017.01)
*C01B 32/194* (2017.01)
*C01B 31/02* (2006.01)
*C01B 31/04* (2006.01)
*B82Y 30/00* (2011.01)
*B82Y 40/00* (2011.01)

(52) U.S. Cl.
CPC ........ *C01B 32/152* (2017.08); *C01B 31/0213* (2013.01); *C01B 31/0273* (2013.01); *C01B 31/04* (2013.01); *C01B 31/0484* (2013.01); *C01B 32/174* (2017.08); *C01B 32/194* (2017.08); *C01B 32/20* (2017.08); *C07D 207/333* (2013.01); *C09C 1/56* (2013.01); *B82Y 30/00* (2013.01); *B82Y 40/00* (2013.01); *C01B 2202/24* (2013.01); *C01B 2202/26* (2013.01); *C01P 2002/82* (2013.01); *C01P 2002/84* (2013.01); *C01P 2002/87* (2013.01); *C01P 2004/32* (2013.01); *C01P 2004/64* (2013.01); *C01P 2006/12* (2013.01); *C01P 2006/19* (2013.01)

(58) Field of Classification Search
CPC .............................. C07D 207/33; C01B 32/152
See application file for complete search history.

(56) References Cited

U.S. PATENT DOCUMENTS

| 2006/0045838 | A1 | 3/2006 | Lucien Malenfant et al. |
| 2012/0112133 | A1 | 5/2012 | Bahnmüller et al. |
| 2015/0210549 | A1 | 7/2015 | Johansson et al. |

FOREIGN PATENT DOCUMENTS

| EP | 2 213 369 | 8/2010 |
| WO | WO 2010/102763 | 9/2010 |
| WO | WO 2013/132352 | 9/2013 |

OTHER PUBLICATIONS

Rahmat et al.; "Carbon Nanotube-Polymer Interactions in Nanocomposites: A Review", Composites Science and Technology, vol. 72, pp. 72-84, (2011).
Potts et al.; "Graphene-Based Polymer Nanocomposites", Polymer, vol. 52, No. 1, pp. 5-25, (2011).
Bokobza; "Multiwall Carbon Nanotube Elastomeric Composites: A Review", Polymer, vol. 48, pp. 4907-4920, (2007).
Galimberti et al.; "The Role of CNTs in Promoting Hybrid Filler Networking and Synergism With Carbon Black in the Mechanical Behavior of Filled Polyisoprene", Macromolecular Materials and Engineering, vol. 298, p. 241-251, (2013).
Galimberti et al.; "Filler Networking of a Nanographite With a High Shape Anisotropy and Synergism With Carbon Black in Poly(1,4-CIS-Isoprene)-Based Nanocomposites", Rubber Chemistry and Technology, vol. 87, No. 2, pp. 197-218, (2014).
Tummala et al.; "SDS Surfactants on Carbon Nanotubes: Aggregate Morphology", ACS Nano, vol. 3, No. 3, pp. 595-602, (2009).
Liu et al.; "Decoration of Carbon Nanotubes With Chitosan", Carbon, vol. 43, pp. 3178-3180, (2005).
Collard et al.; "Lamellar Conjugated Polymers by Electrochemical Polymerization of Heteroarene-Containing Surfactants: Potassium 3-(3-Alkylpyrol-1-yl)Propanesulfonates", Chem. Mater., vol. 6, pp. 850-857, (1994).
Bae et al.; "A Water-Soluble and Self-Doped Conducting Polypyrrole Graft Copolymer", Macromolecules, vol. 38, pp. 1044-1047, (2005).
Jang et al.; "Synthesis and Characterization of Water Soluble Polypyrrole Doped With Functional Dopants", Synthetic Metals, vol. 143, pp. 289-294, (2004).

(Continued)

*Primary Examiner* — Shawquia Jackson
(74) *Attorney, Agent, or Firm* — Finnegan, Henderson, Farabow, Garrett & Dunner, L.L.P.

(57) ABSTRACT

An adduct consists of derivatives of serinol pyrrole and of carbon allotropes in which the carbon is sp² hybridized, such as carbon nanotubes, graphene or nano-graphites or carbon black, in order to improve the chemical-physical properties of the allotropes increasing above all their dispersibility and stability in liquid media and in polymer matrices, and a process for preparation of the adduct.

9 Claims, 8 Drawing Sheets

(56) References Cited

OTHER PUBLICATIONS

Andreeßen et al.; "Serinol: Small Molecule—Big Impact", AMB Express, vol. 1, No. 12, pp. 1-6, (2011).
L. Knorr; Chem. Ber., vol. 18, pp. 299-311, (1885).
C. Paal; Chem. Ber., vol. 18, pp. 367-371, (1885).
Swartzendruber; "Four-Point Probe Measurement of Non-Uniformities in Semiconductors Sheet Resistivity", Solid-State Electronics, vol. 7, pp. 413-422, (1964).
Broadbent et al.; "Novel Heterotricyclic Systems: 2,6-Dioxa- and 2-Oxa-6-Thia-10-Azatricyclo-[5.2.1.0$^{4,1}$ $^0$]Decanes: 2,6-Dioxa-1 1-Azatricyclo[5.3.1.0$^{4,1}$ $^1$]Undecane; and 9, 13-Dioxa-14-Azatetracyclo[6.5.1.0$^{2,7}$0. $^{11,14}$]Tetradeca-2.4.6-Triene (1a, b)" Journal of Heterocyclic Chemistry, vol. 13, pp. 337-348, (1976).
Burnham et al.; "Synthesis Via Modifications of the Knorr-PAAL Procedure: A Derivatives of 2, 6-Dioxa-10-Azatricyclo[5.2.1.0$^{4,1}$ $_0$]Decane. B. Highly Sterically Crowded 1.2.5-Trialkylpyrroles and Pyrrolidines", Chemistry, Dissertation Abstracts, vol. 29, No. 11, pp. 4088B-4089-B, (1969).
International Search Report from the European Patent Office for International Application No. PCT/EP2015/072641, dated Nov. 19, 2015.
Written Opinion of the International Searching Authority from the European Patent Office for International Application No. PCT/EP2015/072641, dated Nov. 19, 2015.
Chun Kiang Chua and Martin Pumer, *Covalent Chemistry on Graphene*, 42 Chem. Soc. Rev. 3222 (2013).
Jin Han and Chao Gao, *Functionalization of carbon nanotubes and other nanocarbons by azide chemistry*, 2(3), Nano-Micro Letters, 213 (2010).

ADDUCTS BETWEEN CARBON ALLOTROPES AND SERINOL DERIVATIVES

CROSS REFERENCE TO RELATED APPLICATIONS

This application is a national phase application based on PCT/EP2015/1072641, filed Sep. 30, 2015, and claims the priority of Italian Patent Application No. MI2014A001714, filed Oct. 1, 2014, the content of each application being incorporated herein by reference,

BACKGROUND OF THE INVENTION

Field of the Invention

The present invention relates to compositions comprising molecules with a pyrrole ring bound to a diol, and carbon allotropes.

In particular, the invention relates to adducts consisting of derivatives of serinol pyrrole and of carbon allotropes in which the carbon is $sp^2$ hybridized, such as carbon nanotubes, graphene or nano-graphites, carbon black, in order to improve the chemical-physical properties of these allotropes increasing above all their dispersibility and stability in liquid media and in polymer matrices.

Description of the Related Art

Currently, one of the research subjects of greatest interest in the field of composite materials concerns the preparation of innovative materials from renewable sources. Key objectives of this activity are: the use of raw materials that do not have an impact on the food cycle both because they do not detract edible raw materials and because they do not use farmland, the implementation of synthesis processes with a low environmental impact both with regard to energy and because they do not use solvents and do not produce waste chemical substances, and the production of composite materials that do not cause problems of disposal after their use.

Among the raw materials from renewable sources, glycerol is of particular interest, as it has no impact on the food cycle, is non-toxic, biodegradable, readily available and low cost. In fact, glycerol is the main by-product of biodiesel synthesis. In 2011, 65% of glycerol was obtained through this process and a total amount of around 1.2 million tonnes was available on the market. Glycerol is considered the main "building block" for the development of an alternative $C_3$ platform to the one deriving from petroleum. Derivatives of glycerol such as serinol are gaining increasing interest, both because glycerol is a pure chemical substance that can be obtained directly from renewable sources and for the chemoselectivity due to the presence of the amine group and of two hydroxyl groups that allow the design and implementation of different synthesis platforms.

It is known that carbon exists in various allotropic forms. Classification of the allotropes can be implemented based on hybridization of the carbon atoms of which this allotrope is formed. In the diamond, the carbon atoms are $sp^3$ hybridized. In other allotropes, the carbon atoms are $sp^2$ hybridized. These are: fullerene, graphene, graphite, carbon nanotubes, carbon black. Fullerene has the form of a hollow sphere, with 12 pentagonal faces and a varying number of hexagonal faces. Graphene is a layer of carbon atoms and therefore has the thickness of one carbon atom. Graphite, carbon nanotubes and carbon black are composed of graphene layers.

Graphite is composed of a variable number of graphene layers stacked in crystalline aggregates, with a typical distance of around 0.34 nm. The number of stacked layers may be less than ten and may reach several thousands. Carbon nanotubes can be viewed as formed of rolled graphene layers. One layer forms the single-wall nanotube, several layers form multiple or multiwall nanotubes. In each of these allotropes, cycles are present as base unit. As mentioned already for fullerene, these cycles can have 5 or 6 carbon atoms, each of which is involved in the formation of three sigma bonds and one π perpendicular to the plane on which the sigma bonds lie. The electrons involved in the π orbital are all delocalized on the aromatic polycyclic system. This is possible because the cycles are all condensed and form a single system. The simplest examples of aromatic polycondensation system are aromatic polycycles (including: pyrene, phenanthrene, anthracene). Fullerene, graphene and carbon nanotubes form the equivalent of aromatic polycondensation system with different degree of planarity. In order for a system to be defined aromatic three conditions must exist: (a) the system must be cyclic, (b) the atoms, involved in the cycle, must all have $sp^2$ hybridization and the sum of the π electrons must satisfy Huckel's rule (π=4n+2, where n is an integer including zero), (c) the system must be planar. In the case of graphene, the requirements are all met. In the case of fullerene and of carbon nanotubes the curvature influences the condition of planarity. These systems can still be defined aromatic and represent an exception.

Carbon allotropes, in which carbon is $sp^2$ hybridized, such as carbon nanotubes, graphene, graphite and carbon black, have electrical and thermal conductivity. In particular, carbon nanotubes and graphene have exceptional mechanical and electrical and thermal conductivity properties. In particular, they are capable of conducting electrons without dissipating energy in the form of heat. Moreover, they have nanometric dimensions, that is, they are smaller than 100 nm: one dimension, in the case of graphene, and two dimensions, in the case of nanotubes. This means they have a large surface area and are therefore capable of establishing a large interfacial area with the matrix in which they are located, greatly influencing its properties. As indicated above, graphite is formed of crystalline aggregates, in turn formed of stacked graphene layers. When the number of stacked graphene layers is low, from less than ten to a few tens, the dimension of the crystalline aggregate in the direction orthogonal to the layers ranges from a few nm to a few tens of nanometers. These graphites are called nano-graphites.

In fact, carbon allotropes can be divided into "nano" and "nano-structured". Carbon allotropes such as fullerene, carbon nano-tubes, graphene and nano-graphites are "nano" allotropes. Carbon black, which has been used for over a century to reinforce elastomeric compounds, is instead "nano-structured". A pure chemical substance is defined "nano" when it has at least one dimension of less than 100 nm. Fullerene, carbon nanotubes, graphene, nano-graphite and their derivatives containing functional groups of different nature and in different amounts are characterized by having at least one dimension of less than 100 nm. Graphene is a layer of $sp^2$ hybridized carbon atoms, has the thickness of a carbon atom and therefore has nanometric dimension. Nano-graphites also have nanometric dimension, provided that the number of stacked graphene layers do not lead to a thickness of over 100 nm. Carbon nanotubes have two nanometric dimensions. Carbon black used as reinforcing filler consists of elementary particles, which have nanometric dimensions, combined to form aggregates in which these elementary particles are held together by covalent bonds. The thermomechanical stresses typical of the action of mixing of the carbon black with elastomeric matrices and also of the use of these matrices are unable to separate the aggregates into elementary components. Aggregation leads to the creation of empty spaces between elementary particles, creating a particular structure for the carbon black. The larger the number of empty spaces, the larger the structure is. This gives rise to the definition of nanostructured filler. Carbon black aggregates have dimensions greater than 100 nm. The aggregates then combine through van der Waals forces to create agglomerates, which can however be separated into the initial aggregates through thermal-mechanical stresses.

Due to their properties, carbon allotropes such as carbon nano-tubes, graphene and nano-graphites and carbon black are used both in polymer, plastic and elastomeric matrices and in coating layers. They promote mechanical reinforcement and thermal and electrical conductivity of the materials in which they are found. Improvement of the aforesaid properties is particularly marked when "nano" carbon allotropes, such as carbon nano-tubes, graphene and nano-graphites are used. Moreover, carbon allotropes such as carbon nano-tubes, graphene and nano-graphites in polymer matrices have a noteworthy flame retardant effect. In the case of polymer matrices, carbon allotropes can be mixed directly in these matrices, forming the final product through conventional mixing technologies, or can be part of predispersions, typically in concentrations greater than those used in the final product. Likewise, in the case of dispersions in liquid media, carbon allotropes can be part of the final formulation, to be used, for example, to form coating layers, or can be in a "masterbatch dispersion" to be used for the preparation of various formulations.

In the case of composite polymer materials containing carbon allotropes, an attempt is made to obtain optimal distribution and dispersion of the allotropes and above all to produce optimal interaction of the allotropes with the matrix and stable interaction in the conditions of use of the material. In the case of dispersions in liquid media, an attempt is made above all to obtain stability of this dispersion, preventing decantation of the allotrope. In fact, the greatest problem that can occur in the case of polymer composite materials containing carbon allotropes is insufficient interaction of the allotropes with the polymer matrix. This problem has been found in particular for "nano" carbon allotropes, such as carbon nano-tubes, graphene, nano-graphites. This leads to insufficient transfer of the properties of the allotropes to the composite material and leads to instability of the dispersion of these allotropes, which tend to aggregate, with considerable worsening of the properties of the final material. The greatest problem that can occur in the case of dispersions of carbon allotropes in both polar and apolar media, consists in the fact that these dispersions are not sufficiently stable to be used in industry, as the carbon allotropes tend to sediment. This problem has been found in particular for "nano" carbon allotropes, such as carbon nano-tubes, graphene, nano-graphites. The polar media can be low viscosity liquids such as solvents of normal use, in particular environmental friendly solvents, such as water, alcohols, ketones and esters. Examples of alcohols are ethanol and isopropanol, examples of ketones are acetone and methyl ethyl ketone, an example of ester is ethyl acetate, an example of amide is N-methyl-pyrrolidone, or can also be low viscosity liquids such as solvents of normal use, specifically those that are environmentally friendly, such as water, alcohols, ketones and esters.

Moreover, the polar media can be polymers, both amorphous and semi-crystalline. These polymers can have a group of polar nature in one or in all the repetitive units. Examples of polymers with a polar group in each repetitive unit are, for example: polyurethanes, polyethers, polyesters, polycarbonates, poly(vinyl esters), poly(vinyl alcohol). Examples of polymers that do not contain a polar group in each repetitive unit are, for example: copolymers of ethylene with polar monomers such as vinyl acetate, vinyl(alcohol). Other examples of polymers that do not contain a polar group in each repetitive unit are polymers in which the polar group has been introduced by means of grafting reaction. Examples of these polymers on which the grafting reaction can be obtained are polyolefins, such as poly(ethylene) and the poly(propylene), ethylene-propylene copolymers, polymers deriving from dienes, on which an anhydride such as maleic anhydride or itaconic anhydride have been grafted, or on which an ester such as ethyl maleate has been grafted, or on which a mixture of an anhydride and an ester has been grafted. There are also polymers that have apolar nature, but contain polar groups as chain terminals, such as natural rubber, i.e. poly(1,4-cis-isoprene) deriving from the plant *hevea brasiliensis*.

"Carbon nano tube-polymer interactions in nanocomposites: A review, Composites Science and Technology 72 (2011) 72-84" describes carbon nano-tube based composites. Graphene based composites and nano-graphites are described in "Graphene-based polymer nanocomposites." Polymer, 52(1), 5-25 (2011)". In these two cases, carbon allotropes are used to prepare composites both in polar polymers such as polyacrylates and epoxy resins and in apolar polymers such as poly(ethylene) and poly(styrene). Dispersions of carbon nano-tubes in elastomeric matrices are described in "Multiwall carbon nanotube elastomeric composites: a review" Polymer, 48(17), 4907-4920 (2007) and in "The Role of CNTs in Promoting Hybrid. Filler Networking and Synergism with Carbon Black in the Mechanical Behavior of Filled Polyisoprene" *Macromol. Mater. Eng.*, 298, 241-251 (2012). Dispersions of nano-graphites are also reported in elastomeric matrices, for example in "Filler Networking Of A Nanographite With A High Shape Anisotropy And Synergism With Carbon Black In Poly(1,4-Cis-Isoprene)—Based Nanocomposites" Rubber Chemistry and Technology, Vol. 87, No. 2, pp. 197-218 (2014). However, all these composites show carbon allotropes dispersed at the level of the single particles of which they are formed, that is, at the level of the single nanotubes or single graphene lamellae or aggregates with only a few graphene layers, but also show agglomerates. In particular, "Filler Networking Of A Nanographite With A High Shape Anisotropy And Synergism With Carbon Black In Poly(1, 4-Cis-Isoprene)—Based Nanocomposites" Rubber Chemistry and Technology, Vol. 87,-); 2, pp. 197-218 (2014) shows how the nano-graphite aggregates tend to aggregate further, that is, to be composed of several graphene layers, when they are in the cross-linked elastomeric composite.

It is known that elastomers cannot be used for practical applications unless they are vulcanized and are reinforced through the addition of reinforcing fillers. For over a century carbon black has been the carbon allotrope of reference for reinforcing elastomers. To be able to perform the reinforcing action of an elastomeric matrix, a filler must not be soluble in the polymer matrix and must have a modulus significantly higher than that of this matrix and have sub-micrometric dimension above all of the particles of which it is formed and, preferably, also of the aggregates of these particles. In fact, the smaller this dimension, the larger the surface area, which means interfacial area with the polymer matrix. In fact, the interfacial area is given by the product of the properties of the filler such as surface area, density and fraction in volume. An extensive interface and good interaction between the reinforcing filler and the polymeric chains are therefore prerequisites for mechanical reinforcement, as they allow stress transfer to the polymer matrix, capable of storing energy. It is therefore evident how "nanofillers" have great potential, due to their intrinsic modulus, to their nano-size and consequent high surface area. Moreover, it is known how the surface area is responsible for mechanical reinforcement with low strains. In fact, a high surface area promotes extensive interaction, which however could be due only to van der Waals forces, thus promoting low strain mechanical reinforcement, which is eliminated as this strain increases. The force applied to increase the strain eliminates van der Waals interactions between the filler and the polymer matrix. The high strain reinforcement is due to stable interaction between the polymer matrix and the filler. The structure of the filler, that is, the voids between the elementary particles of this filler, play a fundamental role in promoting this reinforcement. These voids receive the elastomer, which is immobilized and, so as to speak, itself transformed into filler. In the case of carbon black, "nano-structured" filler, in the presence of a smaller surface area there is less low strain mechanical reinforcement, whereas in the presence of a high structure (and many carbon blacks have a high structure) high strain mechanical reinforcement occurs. Therefore, both "nano" and "nano-structured" carbon allotropes have the prerequisites to perform an important mechanical reinforcing action of the elastomeric matrices. The prior art teaches that the surface tension of the reinforcing filler and of the polymer that forms the matrix cannot be too different in order to obtain effective interaction.

To produce an effective reinforcing action, the fillers must be used in considerable amounts. Typically, in standard ASTM compounds more than 30 parts of filler per 100 parts of elastomer are used. With this amount of filler, the filler is over its percolation threshold, and therefore forms a network. This generates energy dissipation mechanisms essentially due to the absence of weak interactions between filler aggregates, that is, the absence of the network, following the application of static and dynamic mechanical stresses. It is known how the elastic modulus of a filled composite material, to which sinusoidal stresses have been applied, decreases, passing from minimum strain up to around 25% of strain (limit estimated for linear behavior). This phenomenon is known as the "Payne Effect", and is an indicator of the energy dissipation of the material. Decrease of the Payne effect, that is, of energy dissipation in a composite material, passes through the optimization of dispersion of the carbon allotrope, separating them to the smallest individual unit that can be obtained. In order to obtain stable dispersion both in liquid dispersion media with medium-low viscosity and in polymers, the carbon allotropes must be modified both through chemical modifications that lead to the formation of covalent bonds with functional groups, producing functionalizations of the allotropes, and through noncovalent chemical modifications, that is, supramolecular interactions.

WO2010/102763 describes semi-crystalline polyurethane compositions in which carbon nanotubes are dispersed in order to improve their properties. In this case the modifications take place through the use of polymer chains grafted to the carbon allotrope that allow dispersion in polyurethane. However, in this case interaction between the polyurethane and the allotrope is not stable as it occurs only due to carbon group present in the polymer. In the absence of a stable interaction, the carbon nanotube dispersed in the polymer matrix, or in a liquid medium, tends to sediment and to separate from the medium, creating areas with a higher concentration of nanotubes and areas with no nanotubes, consequently changing the properties of the product.

US2006/0045838 describes adducts between carbon nanotubes and soluble polymers selected from poly(thiophene), poly(pyrrole), poly(fluorene), poly(phenylene), poly(phenylene ethynylene), poly(phenylene vinylene), poly(alkylidene fluorene), poly(fluorenebithiophene) and combinations thereof. Also in this case, the modifier is of polymer nature. The nature of the polymers is clearly lipophilic and this implies the choice of organic solvents such as chloroform for their dissolution, solvents that have criticalities from the point of view of impact on the environment and on health. Moreover, these adducts are unable to provide stable dispersions in polar solvents with low environmental impact, such as aqueous solvents. Moreover, the lack of stability of these adducts leads to non-homogeneous dispersion of the nanotubes.

The possibility of dispersing carbon allotropes in aqueous solvents is also known. Surfactants such as sodium dodecyl sulfate are used, as reported in "SDS Surfactants on Carbon Nanotubes: Aggregate Morphology" ACS Nano, 2009, 3 (3), pp. 595-602. In this case, advantage is drawn from the interaction between the dodecyl substituent and the allotrope, while the salt ensures dispersion in water. "Decoration of carbon nanotubes with chitosan" Carbon, 43(15), 3178-3180 (2005) shows the dispersion of carbon nanotubes in acid solutions (pH =5) preparing the adduct of the carbon nanotubes with chitosan. In this case, interaction between the ammonium cations and the π systems of the nanotubes is exploited. It is evident how these modifiers reduce the properties of the allotropes, not contributing to any extent to the electrical and thermal conductivity of these allotropes.

The possibility of solubilizing a polymer with aromatic monomer in an aqueous environment is also known. For example, a water soluble polymer of a pyrrole substitute is obtained by means of electro-oxidative polymerization of potassium 3-(3-alkylpyrrol-1-yl)propanesulfonates, as reported in "Lamellar Conjugated Polymers by Electrochemical Polymerization of Heteroarene-Containing Surfactants: Potassium 3-(3-Alkylpyrrol-1-yl) propanesulfonates" Chem. Mater. 1994,6, 850-851.

A water soluble polypyrrole is reported in "A Water-Soluble and Self-Doped Conducting Polypyrrole Graft Copolymer", *Macromolecules* 2005, 38, 1044-1047. A poly copolymer (sodium styrenesulfonate-co-pyrrolylmethylstyrene) is used as precursor for polymerization of the pyrrole contained as side group in the polymer with other units of non-substituted pyrrole.

In these two examples, synthesis of a substituted pyrrole or of a polymer containing a pyrrole ring is necessary. The yields of these reactions are not high and are not conducted using ingredients from renewable sources. Otherwise, the post treatment of polypyrroles is reported in "Synthesis and characterization of water soluble polypyrrole doped with functional dopants" Synthetic Metals 143 289-294 (2004). Sulfonation of a polypyrrole is performed. In this case, it is not possible to obtain a polymer containing aromatic rings such as that of pyrrole and polar groups directly through polymerization.

It would be desirable to be able to prepare stable dispersions of carbon allotropes both in liquid media and in polymer matrices, producing adducts of carbon allotropes with compounds that contain functional groups capable of interacting with the aromatic rings of the carbon allotropes, consequently groups containing π electrons such as aromatic or carbonyl rings, or ammonium groups, or also only lipophilic groups, without however compromising the possibility of dispersing the adducts in matrices and in polar solvents. In particular, it would be desirable to be able to use solvents with low environmental impact such as alcohols, ethers, esters and even aqueous solvents.

It would be desirable to obtain compounds that comprise both the functional group that promotes interaction with the carbon allotrope and other functional groups. That is, it would be desirable to produce compounds from the molecule containing the functional group capable of interacting with the carbon allotrope.

It would also be desirable to be able to obtain a synergy between the functional groups capable of interacting with carbon allotropes, being able, for example, to combine aromatic rings and other functional groups containing π electrons, such as carbonyls.

It would be desirable for the modifying agents used to prepare the adducts not to reduce the properties of carbon allotropes. In particular, it would be highly desirable for the modifying agents to contribute to the electrical conductivity.

Moreover, it would be desirable for the stable adducts of polymers with carbon allotropes to be easily achievable. In particular, it would be desirable to be able to use simple synthesis and preparation techniques. It would also be desirable to be able to used different preparation methods.

It would be desirable for the structures used to allow stable dispersions of carbon allotropes to be obtained, in order to maintain their properties over time.

Therefore, it would be desirable for the stable dispersions of allotropes in liquid media or in polymer matrices to be easy to produce.

It would be desirable for the compounds capable of interacting stably with carbon allotropes such as nanotubes, graphene and nano-graphites to be produced from renewable sources, which preferably have no impact on the food cycle, so as to obtain a low environmental impact, in terms of energy required for preparation, both because they do not use solvents and do not produce discarded chemical substances, and in terms of disposal of the materials after their use.

An object of the present invention is therefore to provide stable adducts between a carbon allotrope in which the carbon is $sp^2$ hybridized and a compound containing functional groups capable of interacting with the aromatic rings of carbon allotropes.

Yet another object of the present invention is to provide compositions that are easy to obtain, produced from renewable and natural sources that have no impact on the food cycle so as to obtain materials with a low environmental impact both in terms of energy linked to their preparation and in terms of pollution caused by their disposal.

Moreover, an object of the present invention is to provide compounds capable of interacting with carbon allotropes in a stable and efficient manner and that do not compromise the possibility of dispersing carbon allotropes also in polar solvents, even water-based.

Moreover, an object of the present invention is to provide structures capable of interacting with carbon allotropes in a stable and efficient manner and that can, to some extent, contribute to the properties of the carbon allotrope, such as electrical conductivity.

SUMMARY OF THE INVENTION

These and other objects of the present invention are achieved by means of the adduct of a compound of formula (I)

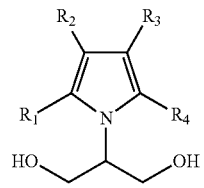

wherein $R_1$, $R_2$, $R_3$, $R_4$ are independently selected from the group consisting of: hydrogen, C1-C3 alkyl, $C_2$-$C_{22}$ linear or branched alkenyl or alkynyl, aryl, $C_1$-$C_{22}$ linear or branched alkyl-aryl, $C_2$-$C_{22}$ linear or branched alkenyl-aryl, $C_2$-$C_{22}$ linear or branched alkynyl-aryl, heteroaryl,
and a carbon allotrope or its derivatives.

In this way, a compound is obtained containing allotropes capable of being dispersed in numerous matrices, and of being used in processes where it is necessary to maintain the properties of these allotropes.

Preferably said $R_1$, $R_2$, $R_3$, and $R_4$ are independently selected from the group consisting of: H, $CH_3$, $CH_2CH_3$, phenyl.

Preferably, the carbon allotrope or its derivative is selected from the group consisting of: carbon black, fullerene, single-wall or multiwall carbon nanotubes, graphene, graphite with a number of graphene layers from 2 to 10000.

Preferably, said carbon allotrope derivative contains functional groups, selected from the group consisting of:
oxygenated functional groups, preferably hydroxyl, epoxy;
functional groups containing carbonyl, preferably aldehydes, ketones, carboxylic acids;
functional groups containing nitrogen atoms, preferably amines, amides, nitriles, diazonium salts, imines;
functional groups containing sulfur atoms, preferably sulfides, disulfides, mercaptans, sulfones, sulfonic and sulfinic groups.

In this way a vast range of carbon allotropes is available.

Preferably, the carbon allotrope derivative is graphite oxide or graphene oxide.

A further object of the present invention is to provide a process for the preparation of an adduct according to one or more of the preceding claims comprising the steps of:
i. providing a solution of a compound of formula (I) in a protic or aprotic polar solvent;
ii. providing a suspension of the carbon allotrope in the protic or aprotic polar solvent used for the preparation of the solution referred to in step i;
iii. mixing said solution and said suspension;
iv. removing said solvent from the mixture obtained in step iii.;
v. providing thermal and/or mechanical energy and/or photon irradiation energy to the mixture obtained.

Preferably, the thermal energy is provided at a temperature from 50 to 180° C. and for a time from 15 to 360 minutes.

Preferably, the mechanical energy is provided for a time from 15 to 360 minutes.

Preferably, the photon irradiation energy is provided at a wavelength from 200 to 380nm and for a time from 30 to 180 minutes.

The method for the preparation of the adduct according to the present invention, starting from synthesis of the starting monomers, will now be described.

According to the present invention, the compositions described were obtained by synthesizing the compound of formula (I) starting from 2-amino-1,3-propanediol, known as serinol (formula III)

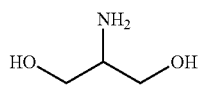

(III)

or from a substituted serinol of general formula:

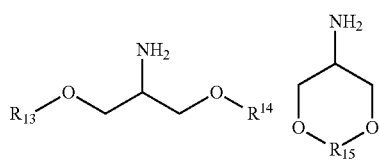

wherein R13 and R14 are independently selected from the group consisting of: hydrogen, C1-C22 alkyl, C2-C22 linear or branched alkenyl or alkynyl, aryl, C2-C22 linear or branched alkyl-aryl, C2-C22 linear or branched alkenyl-aryl, C2-C22 linear or branched alkynyl-aryl, heteroaryl.

Serinol is commercially available, but can be prepared from glycerol or from dihydroxyacetone, or can be obtained directly from renewable sources, such as from glycerol, dihydroxyacetone or from dihydroxyacetone oxime as indicated in "Serinol: small molecule—big impact" AMB Express 2011, 1:12.

In order to obtain the compound of formula (I) serinol is reacted with a diketone of general formula

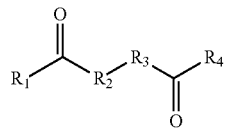

wherein $R_1$, $R_2$, $R_3$, $R_4$ are independently selected from the group consisting of: hydrogen, C1-C22 alkyl, $C_2$-$C_{22}$ linear or branched alkenyl or alkynyl, aryl, $C_1$-$C_{22}$ alkyl-aryl, $C_2$-$C_{22}$ linear or branched alkenyl-aryl, $C_2$-$C_{22}$ alkynyl-aryl, heteroaryl.

By way of example, there is described below the preparation of a derivative of the serinol of formula (I), namely 2-(2,5-dimethyl-1H-pyrrol-1-yl)-1,3-propanediol (formula V), through a two-stage process, as described below.

2-amino-1,3-propanediol is reacted with 2,5-hexanedione in equimolar amounts, obtaining the tricyclic compound 4a,6a-dimethyl-hexahydrate-1,4-dioxa-6b-azacyclopenta[cd]pentalene (formula IV)

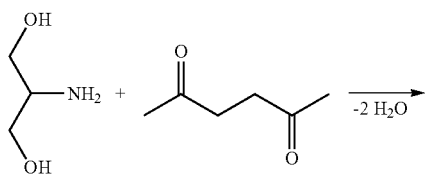

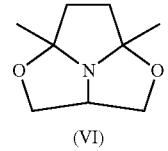

(VI)

Synthesis of the compound of formula (IV) is produced through the Knorr-Paal reaction (L. Knorr, Chem. Ber., vol. 18, p. 299 (1885); C. Paal, Chem. Ber., vol. 18, p. 367 (1885); H. Smith Broadbent, Journal of Heterocyclic Chemistry, vol. 13, pp. 337-348 0(1976).). The reaction can also be conducted without solvents and without the addition of catalysts, obtaining a high yield (around 99%) at ambient temperature, and with reaction time of around 6 hours.

The compound of formula (IV) is then heated to a temperature from 170 to 190° C. for a time from 40 to 60 minutes, obtaining the compound of formula (V)

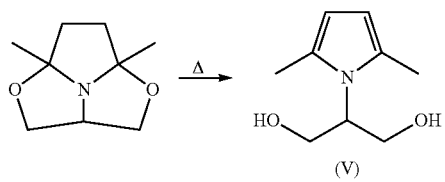

(V)

In particular, the compound of formula (V), 2-(2,5-dimethyl-1H-pyrrol-1-yl)-1,3-propanediol, hereinafter called serinol pyrrole (SP), is obtained by isomerization of the compound of formula (IV) by heating and subsequently isolated by distillation at reduced pressure obtaining a total yield of the synthesis of around 85%.

The carbon fillers according to the present invention are carbon allotropes in which the carbon is $sp^2$ hybridized. In particular, these are: fullerene, graphene, graphite, carbon nanotubes, carbon black. According to the present invention, the carbon allotropes can contain functional groups selected from the group consisting of:
  oxygenated functional groups, preferably hydroxyl, epoxy;
  functional groups containing carbonyls, preferably aldehydes, ketones, carboxylic acids;
  functional groups containing nitrogen atoms, preferably amines, amides, nitrites, diazonium salts, imines;
  functional groups containing sulfur atoms, preferably sulfides, disulfides, mercaptans, sulfones, sulfonic and sulfinic groups.

Preferably, according to the present invention the carbon allotrope is graphite oxide or graphene oxide.

Carbon fillers defined nano, such as fullerene, carbon nanotubes, graphene, nano graphite and their derivatives containing functional groups of different nature and in different amounts are characterized by having at least one dimension of less than 100 nm. Graphene is a layer of $sp^2$ hybridized carbon atoms, has the thickness of one carbon atom and therefore has nanometric dimension. Nano-graphites also have nanometric dimension, provided that the number of stacked graphene layers do not lead to a thickness greater than 100 nm. Carbon nanotubes have two nanometric dimensions. Nanofillers are characterized by the possibility of separating the aggregates or agglomerates into elementary constituent particles. Carbon nanotubes, whether single-wall or multiwall, are intertwined in a mass. The individual tubes can be separated from the mass in which they are intertwined. It is also possible to perform exfoliation of a graphite having a different initial number of stacked layers, obtaining nano-graphites with a low number of stacked layers and also graphene. Graphites with a low number of stacked layers have nanometric dimensions and are called nano-graphites.

Carbon allotropes, being more or less reactive aromatic systems, are subject to various types of intermolecular interactions.

They are stacked on one another. A stacked arrangement of aromatic molecules is defined as stacking. In fact, molecules containing aromatic rings tend to arrange themselves spontaneously stacked on one another. This gives rise to the concept of aromatic interaction (or π-π (interaction), which is intended as a bond of noncovalent type established between organic compounds containing aromatic groups, due to intermolecular overlap of p orbitals in π-conjugated systems. This type of interaction makes the bond even more stable, as it increases the number of π electrons.

Carbon allotropes can also give rise to intermolecular interactions with the formation of covalent bonds. These intermolecular interactions with the formation of covalent bonds are typical of aromatic polycyclic systems. For example, they are: 1,3-dipolar cycloadditions, Diels-Alder reaction.

According to the present invention, compositions are obtained in which there are stable interactions between carbon allotropes and serinol pyrrole or its variously substituted derivatives. Five-membered heterocyclic rings, such as pyrrole, are defined as electron-rich as the aromatic cycle has 5 atoms and 6 π electrons. The electron density per atom is therefore greater than a benzene ring. Their pentagonal structure and the presence of the heteroatom give greater instability to the system, which is therefore more reactive with respect to benzene. It is known that of the three electron-rich heterocycles, in terms of reactivity pyrrole is midway between furan and thiophene. Electron rich heterocycles are less reactive than dienes but more reactive than benzene. In fact, they are able to give reactions typical of electron-rich dienes.

These electron-rich heterocyclic rings can give rise to interactions with carbon allotropes with the formation both of noncovalent bonds and of covalent bonds.

In particular, in the composition according to the present invention, serinol pyrrole or a derivative thereof and carbon allotrope are in the form of adduct.

According to the present invention the term adduct is intended as a compound obtained by means of an addition reaction; more specifically, those particular addition compounds whose components, bound more or less unstably, preserve their individuality to some extent are called adducts.

According to the present invention, the addition reaction between the carbon filler, that is, the aromatic polycyclic system, and the electron-rich pyrrole ring of serinol pyrrole is obtained. In the addition reaction, which leads to formation of the adduct, the following two types of interaction can be hypothesized:

(i) π-π interaction. π-π interaction can exist between systems that have π electrons, thus having sp2 or sp hybridization. The interaction is between a pair of π electons and one a orbital, or between the electrons of one a orbital and one π orbital, or again between the electrons of two it orbitals. This type of adduct is also known as "π complex". As indicated above, this type of reaction leads to stacking.

(ii) covalent bonds between the pyrrole ring and the carbon allotrope, through one of the reactions described above.

As indicated above, carbon allotropes, in particular "nano" allotropes such as fullerene, carbon nanotubes, graphene and nano-graphite can contain functional groups of different nature. According to the present invention, the addition reaction between molecules with a pyrrole ring bound to a diol and the carbon allotrope that contains the functional groups is obtained. Formation of the adduct can be obtained through interaction between the pyrrole ring or the hydroxyl groups of the molecule with a pyrrole ring bound to a diol and the functional groups present on the carbon allotrope. The interactions that can give rise to the pyrrole ring have already been indicated above. The interactions that a hydroxyl group can cause can be of intermolecular nature, such as hydrogen bonds and dipole interactions or of covalent nature, such as esterification through reaction with an acid group.

According to the present invention, the adduct that is formed by addition reaction between the carbon allotrope and SP can be reversible. The reversibility of the adduct can be a function of various reaction parameters, such as temperature, time, use of solvents.

There is now described the process for the preparation of an adduct comprising a compound of formula (I)

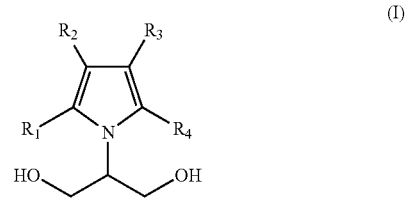

wherein $R_1$, $R_2$, $R_3$, $R_4$ are independently selected from the group consisting of: hydrogen, C1-C3 alkyl, $C_2$-$C_{22}$ linear or branched alkenyl or alkynyl, aryl, $C_1$-$C_{22}$ linear or branched alkyl-aryl, $C_2$-$C_{22}$ linear or branched alkenyl-aryl, $C_2$-$C_{22}$ linear or branched alkynyl-aryl, heteroaryl, and a carbon allotrope or its derivatives.

The process in a possible embodiment thereof, comprises the following steps:

a) preparing a solution of at least a compound of formula (I) in a protic or aprotic polar solvent selected from the group consisting of: water, alcohols, carbonyl solvents such as acetone, esters such as ethylene acetate, dimethyl sulfoxide, acetonitrile, ethers;

b) preparing a suspension of the carbon allotrope in the protic or aprotic polar solvent used to prepare the solution of the compound of formula (I);

c) mixing the solution of the compound of formula (I) and the suspension of the carbon allotrope, using a mechanical or magnetic stirring system, or by means of sonication with sonication equipment, for example using an ultrasonic bath;

d) removing the solvent from the mixture obtained.

With the procedure described in points a)-c) it is possible to obtain a relative homogeneous dispersion of the nanofiller and of at least one serinol derivative containing a pyrrole ring and therefore to obtain a homogeneous dispersion on the carbon filler of the serinol derivative containing a pyrrole ring. The solvents are removed before the successive actions aimed at transferring energy to the adduct between the carbon nanofiller and at least one serinol derivative containing a pyrrole ring.

The term solvent refers to serinol derivatives containing a pyrrole ring of formula (I) and evidently not to the carbon allotrope, for which the solvent only acts as dispersion medium.

The solvent must preferably be environmentally friendly.

Hereinafter in the present description, the terms "carbon allotrope" and "carbon filler" are used interchangeably.

Generally, due to the chemical nature of carbon, dispersion of carbon fillers in liquid matrices is somewhat difficult. The use of ultrasound allows dispersion in reduced times and improves the homogeneity of the dispersion of carbon filler (even a few seconds). Moreover, the use of sonication allows separation, to different extents, of the carbon nanofillers in the elementary units. The carbon nanotubes can be separated into individual tubes from the mass in which they are interwoven with other tubes. The use of low power sonicators, such as classic ultrasonic baths, is advisable. With suitable solvents it is also possible to obtain at least partial exfoliation of a graphite having a different starting number of stacked layers. Graphites with a low number of stacked layers have nanometric dimensions and are called nano-graphites. Therefore, it is preferable for the nanofiller to be preliminarily contacted with a liquid, in order to obtain, through sonication and according to the nanofiller, either unraveling of the carbon nanotubes or an exfoliation, to a greater or lesser extent, of the graphite or nano graphite. This procedure causes an improvement in the contact between the nanofiller and the serinol derivative containing a pyrrole ring, also causing an increase in the exposed area of the nanofiller.

According to the present invention, the term "sonochemistry" indicates the physical-chemical discipline that studies chemical reactions that occur in a solution irradiated by ultrasound. This irradiation gives rise, for an intensity of the range above a given threshold, to a phenomenon of cavitation in the solution. The gaseous microcavities (bubbles) present in the solution, subjected to subsequent expansions and contractions induced by the oscillating sound pressure field, expand and then implode, producing areas of very high temperature and pressure. In these extreme conditions, chemical reactions of considerable interest can occur in the field of synthesis of organic substances, of polymerization processes, and of degradation of toxic and harmful substances. With the application of sonication techniques, it is also possible to obtain amorphous materials that, outside the extreme conditions typical of sonication, would naturally tend to crystallize.

The procedure to remove the solvent, pursuant to point d), from the mixture obtained, can take place using any suitable method for removing solvent, such as vacuum evaporation, spray drying, etc.

The mixture obtained after removing the solvent from the mixture containing the compound of formula (I) and the carbon allotrope, can be subjected to a further step e), in which energy is transferred to the composition.

The addition reaction, which leads to the formation of the adduct, is obtained with transfer of energy to the system formed by the molecule containing the pyrrole ring bound to a diol and by the carbon allotrope. The transfer of energy occurs in order to improve interaction between the molecule containing the pyrrole ring bound to a diol and the carbon allotrope.

If there is no transfer of energy, a weaker interaction between the pyrrole ring bound to the diol and the carbon allotrope is obtained. A weaker interaction causes partial release from the carbon allotrope of the molecule containing the pyrrole ring bound to a diol, especially if the adduct is in a polar environment.

The forms of energy that can be transferred to the composition to allow its formation are:
mechanical energy
thermal energy
photons Mechanical Energy The mixture obtained between the nanofiller and at least one serinol derivative containing a pyrrole ring, obtained through the process described above in steps a-c, ii treated using a mechanical process.

The mechanical treatment consists of placing the powder obtained (nanofiller/SP) in a jar equipped with stainless steel balls. After closing the jar it is placed in a planetary miter and left to rotate at a speed from 200 to 500 rpm for times from 1 to 360 minutes. The powder is decanted immediately afterwards.

The mechanical treatment referred to is used both to induce disorder (exfoliation in the case of graphite) in order to obtain improved SP distribution on the nanofiller, and to induce the formation of a much more stable interaction.

This is possible as the possibility of inducing chemical reactions on dry mixtures by subjecting them to mechanical forces is known in chemistry. Mechanochemistry is a branch of chemistry that is not very well known, but which arouses great interest, given its environmentally friendly nature. A mechanochemical process can be triggered simply by using a mortar and pestle or bulkier systems that operate simply such as ball mills, used both in the pharmaceutical and food industry.

Planetary ball mills contain cylindrical reactors, jars, held in vertical position on a rotating platform. In mills with jars containing balls, the collision between balls, which are typically between 5 and 50 in number, is exploited. The efficiency with which a given mill operates in relation to a given mechanochemical transformation is intimately linked to the frequency of collisions between the balls and the inner wall of the jar and to the mechanical energy transferred. These quantities in turn depend on the dynamics of the balls, on their number and size, on the oscillating, or working, frequency of the mill, and on the total amount of powder inside the reactor.

Thermal Energy

The mixture obtained between the nanofiller and at least one serinol derivative containing a pyrrole ring, obtained through the process described above in steps a-c, is treated by means of a thermal process.

The thermal treatment consists of placing the powder obtained (nanofiller/SP) in a reaction flask provided with coolant or in a sealed vial. After positioning the reactor on a heating plate the reaction is conducted at a temperature from 130 to 180° C. Heating is maintained for a minimum of 2 up to 12 hours. The heat treatment induces the formation of stable interactions.

Photons

The mixture obtained between the nanofiller and at least one serinol derivative containing a pyrrole ring, obtained through the process described above in steps a-c, is treated by means of an irradiation process using a lamp with a suitable wavelength.

The photon treatment consists of placing the powder obtained (nanofiller/SP) in a laboratory crystallizer forming a thin layer or placing the powder in a sealed quartz vial. After positioning the reactor inside a dark room equipped with a 254 nm low pressure mercury lamp (or using a Rayonet$^R$ reactor equipped with the same type of lamp) the mixture is irradiated for times variable from 30 to 180 minutes. After this time the mixture is decanted and analyzed.

With an adduct according to the present invention it is possible to obtain suspensions of carbon nanofillers stable both in aqueous media and in other substrates, such as polymer compounds or rubbers, thus obtaining homogeneous products that have the specific properties of carbon nanofillers, such as high mechanical properties, high electrical conductivity, resistance to high temperatures, flame-retardant properties.

With an adduct according to the present invention it is also possible to obtain uniform and continuous layers of black fillers on different substrates in order to obtain highly conductive surfaces.

Some examples of preparation of the adduct comprising serinol pyrrole or a derivative thereof and a carbon allotrope according to the present invention will be described below.

The adduct according to the present invention will be better illustrated through the examples set down below, which illustrate the operating steps of the process for the preparation of this adduct.

BRIEF DESCRIPTION OF THE DRAWINGS

Characteristics and advantages of the invention will be more apparent from the description of preferred embodiments, shown by way of non-limiting example in the accompanying drawings, wherein.

DETAILED DESCRIPTION OF THE INVENTION

EXAMPLES

Figure 1:
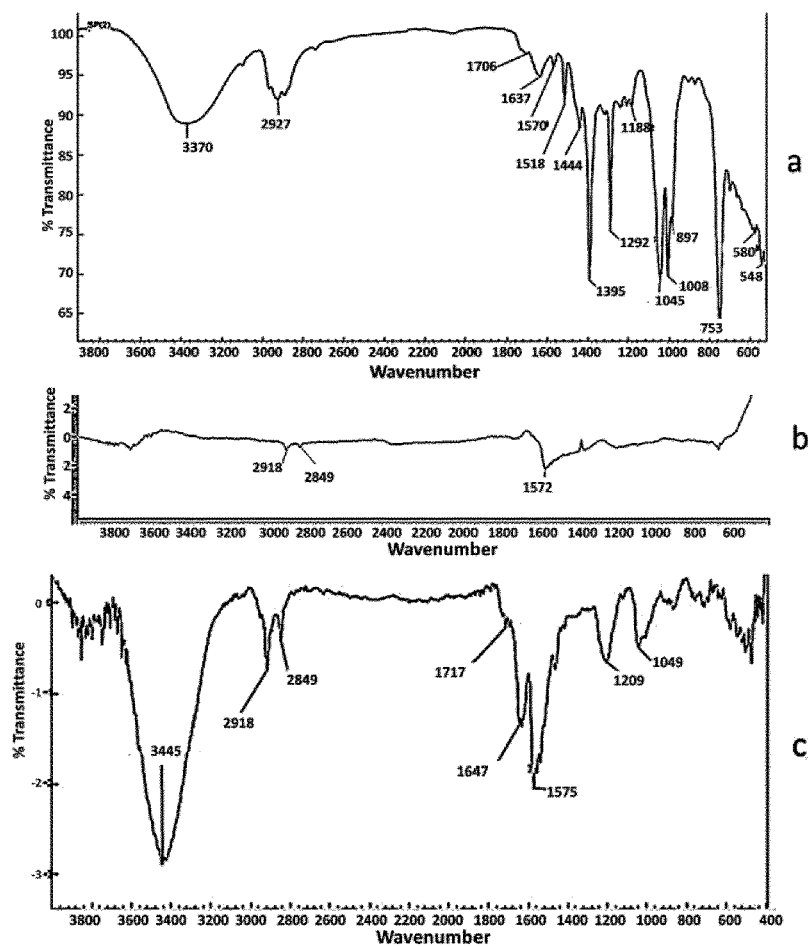
FIG. 1 shows the IR spectrum of the composition according to Example 1.

The compositions obtained by means of the examples indicated below were analyzed as follows:

infrared analysis (FT-IR using KBr pellet): adduct/KBr weight ratios of 1:500 and approximately 80 mg of mixture to form the pellet were used. The pellet was analyzed by means of a Fourier Transform IR spectrophotometer (Varian 640-IR FT-IR spectrometer with ATR option). The samples were irradiated in a range from 2.5 to 20 µm (or from 4000 to 500 cm-1)

UV spectroscopy: the adduct suspensions (3 mL) were placed, using a Pasteur pipette, in quartz cuvettes with a 1 cm optical path length (volume 1 or 3 mL) and analyzed using a UV-Vis spectrophotometer. The instrument was reset with pure solvent and a UV spectrum from 200-340 nm recorded. A blank of the solvent used was recorded. The UV-visible spectrum indicated the absorption intensity as a function of the wavelength of the radiation from 200 to 750 nm.

DLS (Dynamic Light Scattering): the adduct powder was dispersed in water by sonication for 10 minutes. A first analysis was performed collecting the suspended portion (3 mL) and placing it in a quartz cuvette with a 1 cm optical path length (volume 1 or 3 mL). In parallel, the sonicated mixture was placed in a Falcon centrifuge tube. The suspensions were progressively centrifuged and analyzed: (i) 9000 rpm for 5 minutes; (ii) 9000 rpm for 30 minutes. Evaluation of the size distribution by intensity (Intensity %-d. nm) was performed for all samples.

stability in water: after treatment the powder was placed in a laboratory vial, water was added (concentration of 1 mg/mL) and it was sonicated for 10 minutes, after which the extent of decantation was visually evaluated.

Example 1

Adduct of 2-(2,5-dimethyl-1H-pyrrol-1-yl)-1,3-propandiol (called Serinol pyrrole, indicated below as SP) with graphite.

The graphite used was Synthetic Graphite 8427, purchased from Asbury Graphite Mills Inc., with a minimum carbon content of 99.8% by weight and a surface area of 330 m$^2$/g. 10 g of graphite (NanoG) and 50 mL of acetone were fed to a 250 mL one-neck round-bottom flask. The suspension was sonicated in a 2 liter ultrasonic bath with a power of 260 Watts for 15 minutes. After this time, a solution of 2.35 g of SP in 50 mL of acetone was added. The resulting suspension was sonicated for a further 15 minutes. The solvent was removed at reduced pressure. A powder consisting of graphite with adsorbed SP (graphite/SP adduct) was obtained.

12 g of graphite/SP adduct was placed in a stainless steel jar with a capacity of 200 mL and containing 5 stainless steel balls. The jar was placed in a planetary mill and rotated at 300 rpm for successive times: 1 hour, a further 1 hour, a further 1 hour, a further 3 hours. after the milling times indicated 500 mg of powder was collected and washed with water. Washing was performed as follows: 16 mL of water was added to 500 mg of powder. The suspension thus obtained, formed by SP/graphite and water, was sonicated in a 2 liter ultrasonic bath with a power of 260 Watts for 15 minutes. It was then centrifuged at 4000 rpm for 10 minutes, using 15 mL Falcon centrifuge tubes and a benchtop centrifuge (Centrifugette 4206-ALC). The supernatant was removed simply by pouring off. The procedure was repeated until no SP was observed in the wash water. In this example it was repeated 8 times. Verification of the presence of SP in the wash water was performed through TLC and GC-MS analysis. After wash no. 6, the presence of SP on the plate was no longer noted (TLC analysis). GC-MS analysis did not detect the presence of SP. The powder was dried at reduced pressure (70 mmHg) and at 40° C.

The samples of adduct collected after the grinding times indicated and washed as illustrated were characterized by FT-IR analysis performed preparing a pellet of the adduct sample in KBr.

The adduct sample ground for 6 hours was washed according to the procedure indicated and the wash waters were analyzed by UV spectroscopy. The UV spectrum shows no absorption. The washed nanoG sample whose wash waters showed no absorption were analyzed by infrared (IR) spectroscopy. FIG. 1 shows the SP spectrum (FIG. 1 letter a) of the starting nanoG (FIG. 1 letter b), of nanoG after reaction and washing (FIG. 1 letter c). The IR spectrum in FIG. 1-c shows the characteristics SP peaks, confirming the formation of the stable nanoG-SP adduct.

A suspension was also prepared with the sample of nanoG treated with SP after 6 hours of grinding and after washing. The suspension, having a concentration of 1 mg/mL, was sonicated for 10 minutes and analyzed by ultraviolet (UV) spectroscopy. UV spectra were recorded immediately after sonication and after 24 hours and showed the same absorbance.

Figure 2:
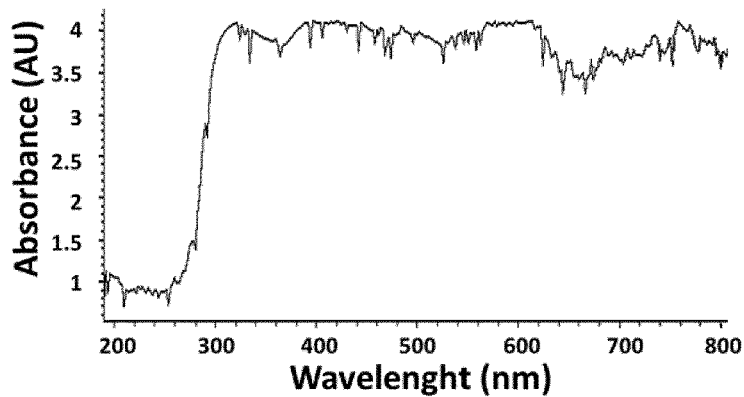
FIG. 2 shows the UV spectrum of the composition according to Example 1.

FIG. 2 shows the spectrum recorded after 24 hours.

The suspension was centrifuged at 2000 rpm, for 5 and for 30 minutes. After centrifugation for 30 minutes, UV analysis showed reduced absorbance with respect to that measured at t=0, without centrifugation.

Example 2

Adduct of SP with graphite.

The example was conducted in the same way as Example 1 but with a nanoG/SP ratio of 1 to 2 in moles. Moles of nanoG are intended as the moles of benzene ring, calculated assuming the nanoG is 100% carbon.

The adduct samples collected after the indicated grinding and washing times as illustrated, were characterized by FT-IR analysis performed preparing a pellet of the adduct sample in KBr.

Figure 3:
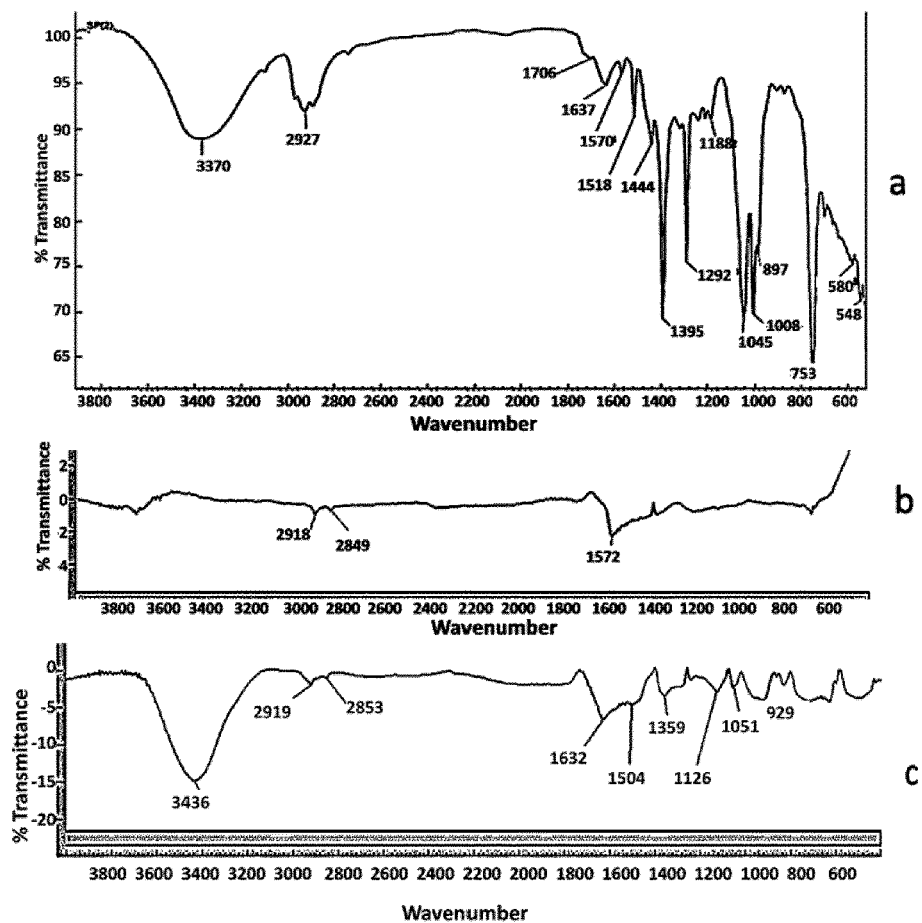
FIG. 3 shows the IR spectrum of the composition according to Example 2.

The adduct sample ground for 6 hours was washed according to the procedure indicated and the wash waters were analyzed by UV spectroscopy. The UV spectrum showed no absorption. The washed nanoG sample whose wash waters showed no absorption were analyzed by infrared (IR) spectroscopy. FIG. 3 shows the SP spectrum (FIG. 3 letter a) of the starting nanoG (FIG. 3 letter b), of nanoG after reaction and washing (FIG. 3 letter c). The IR spectrum in FIG. 3-c shows the characteristic peaks of SP, confirming the formation of the stable nanoG-SP adduct.

Figure 4:
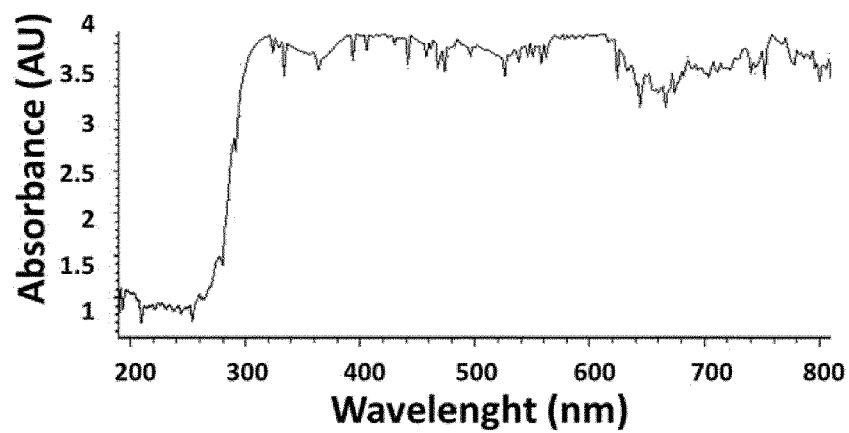
FIG. 4 shows the UV spectrum of the composition according to Example 2.

A suspension was also prepared with the sample of nanoG treated with SP after 6 hours of grinding and after washing. The suspension, having a concentration of 1 mg/mL, was sonicated for 10 minutes and analyzed by ultraviolet (UV) spectroscopy). UV spectra were recorded immediately after sonication and after 24 hours and showed the same absorbance. FIG. 4 shows the spectrum recorded after 24 hours.

Example 3

Adduct of SP with MWCNT.

The multiwall carbon nanotubes (MWCNT) used were NC7000 series by NANOCYL Inc. A suspension of 0.100 g of CNT in 30 mL of acetone was sonicated in a 2 liter ultrasonic bath with a power of 260 Watts for 30 minutes. 15 mL of a solution of acetone containing 0.100 g of SP was added to this suspension. The resulting suspension was sonicated again for 30 minutes. The solvent was removed with a rotary evaporator, obtaining a solid residue. The powder without solvent thus obtained consisted of SP adsorbed on CNT. 0.200 g of this powder was placed in a stainless steel jar with a capacity of 200 mL and containing 5 stainless steel balls. The jar was rotated at 300 rpm for 15 minutes at ambient temperature. 2 mg of the powder thus obtained was placed in $H_2O$ (2 mL) and sonicated for 30 minutes.

A suspension was also prepared with the sample of CNT treated with SP after 15 minutes of grinding and after washing. The suspension, having a concentration of 1 mg/mL, was sonicated for 10 minutes and analyzed by UV spectroscopy. UV spectra were recorded immediately after sonication and after 12 hours and showed the same absorbance.

Example 4

Adduct of SP with Carbon black.

The Carbon black used was Carbon Black N326 (CB) (Cabot), having the following properties: 30 nm average diameter of the spherical particles, surface area of 77 $m^2/g$ (determined by nitrogen absorption), DBP absorption of 85 mL/100 g.

1 g of carbon black and 15 mL of acetone were added to a 100 mL one-neck round-bottom flask. The suspension was sonicated in an ultrasonic bath for 15 minutes. After this time, a solution of 0.235 g of SP in 15 mL of acetone was added. The resulting suspension was sonicated for a further 15 minutes. The solvent was removed at reduced pressure. A powder consisting of carbon black with absorbed SP (CB/SP adduct) was obtained.

0.700 g of CB/SP adduct was placed in a 30 mL vial equipped with magnetic stirrer. The reaction mixture was heated to the temperature of 180° C. for 2 hours. After this time, the powder was cooled to 25° C.

The powder was then placed in a Buchner funnel with filter and washed repeatedly with distilled water. The wash water was colorless. The presence of SP in the wash water was verified by TLC and GC-MS analysis. After wash no. 6, the presence of SP on the plate was no longer noted (TLC analysis). GC-MS analysis did not detect the presence of SP.

The samples of adduct collected after the heating times indicated and washed as illustrated were characterized by FT-IR analysis preparing a pellet of the adduct sample in KBr.

The adduct sample treated for 2 hours at 180° C. was washed according to the procedure indicated and the wash waters were analyzed by UV spectroscopy. The UV spectrum shows no absorption.

Figure 5:
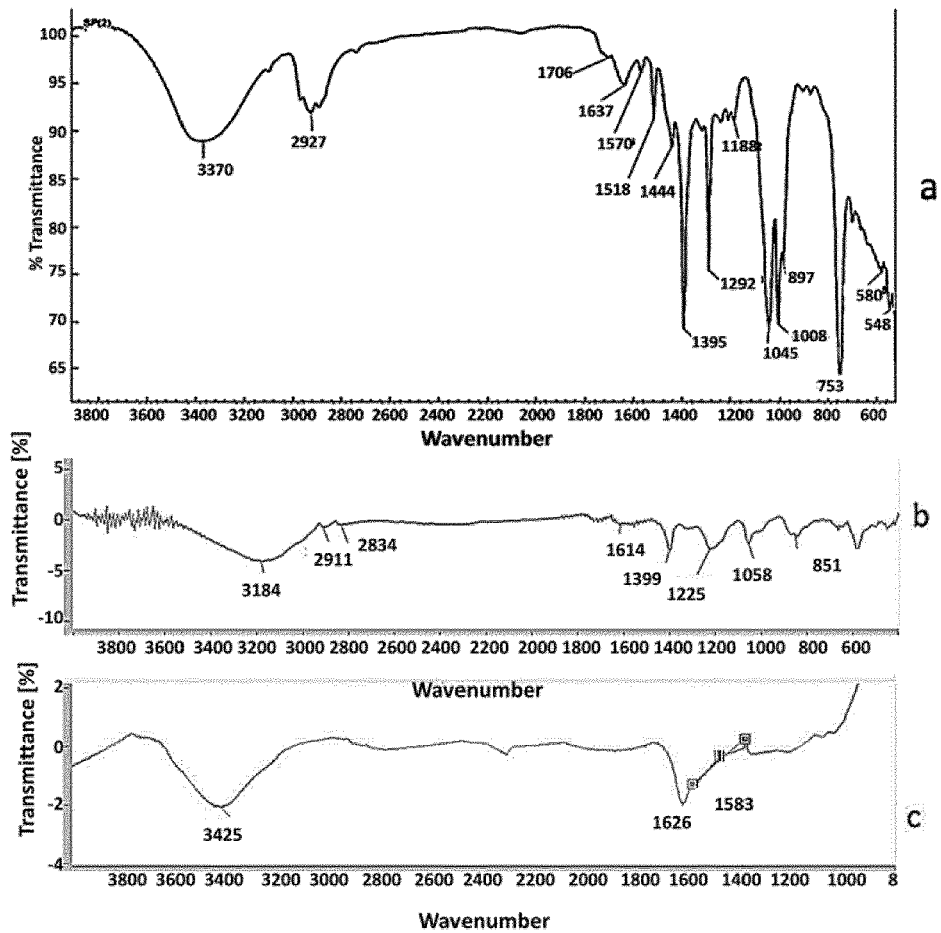
FIG. 5 shows the IR spectrum of the composition according to Example 4.

The washed carbon black sample whose wash waters showed no absorption were analyzed by infrared (IR) spectroscopy. FIG. 5 shows the SP spectrum (FIG. 5 letter a) of the starting carbon black (FIG. 5 letter b), of the carbon black after reaction and washing (FIG. 5 letter c). The IR spectrum in FIG. 5-c shows the characteristic peaks of SP, confirming the formation of the stable Carbon black-SP adduct.

Figure 6:
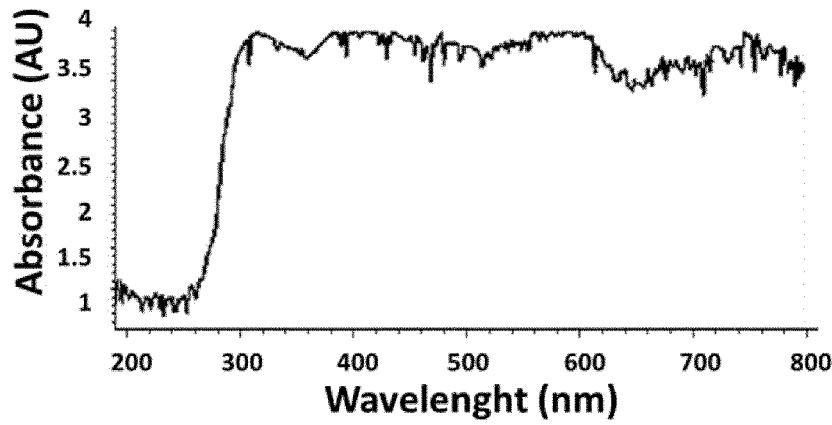
FIG. 6 shows the UV spectrum of the composition according to Example 4.

A suspension was also prepared with the sample of carbon black treated with SP after heating to 180° C. for 2 hours and after washing. The suspension, having a concentration of 1 mg/mL, was sonicated for 10 minutes and analyzed by ultraviolet (UV) spectroscopy. UV spectra were recorded immediately after sonication and after 24 hours and showed the same absorbance. FIG. 6 shows the spectrum recorded after 24 hours.

Figure 7:
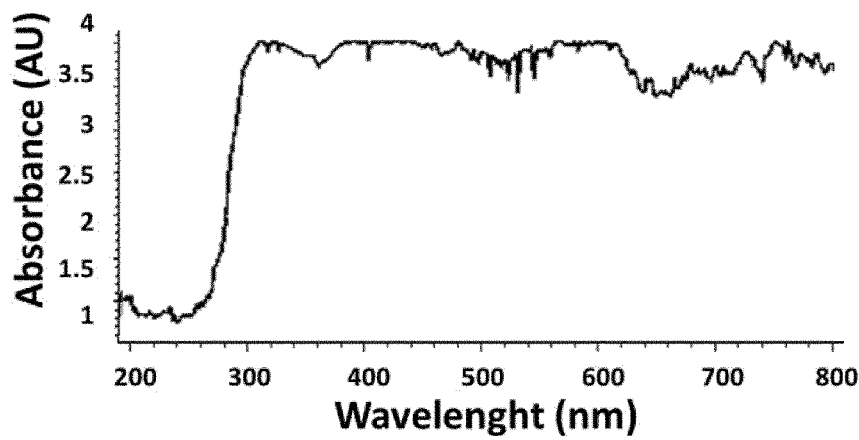
FIG. 7 shows the UV spectrum of the composition according to Example 4.

The suspension was then centrifuged at 2000 rpm, for 5 and for 30 minutes, without observing any reduction of absorbance in the UV absorption spectrum as shown in FIG. 7.

Example 5

Adduct of SP with Carbon black.

The example was conducted in the same was as Example 4 but with Carbon black/SP ratios of 1 to 2 in moles. Moles of carbon black are intended as the moles of benzene ring, calculated assuming the carbon black is 100% carbon.

The adduct sample treated for 2 hours at 180° C. was washed according to the procedure indicated and the wash waters were analyzed by UV spectroscopy. The UV spectrum shows no absorption.

Figure 8:
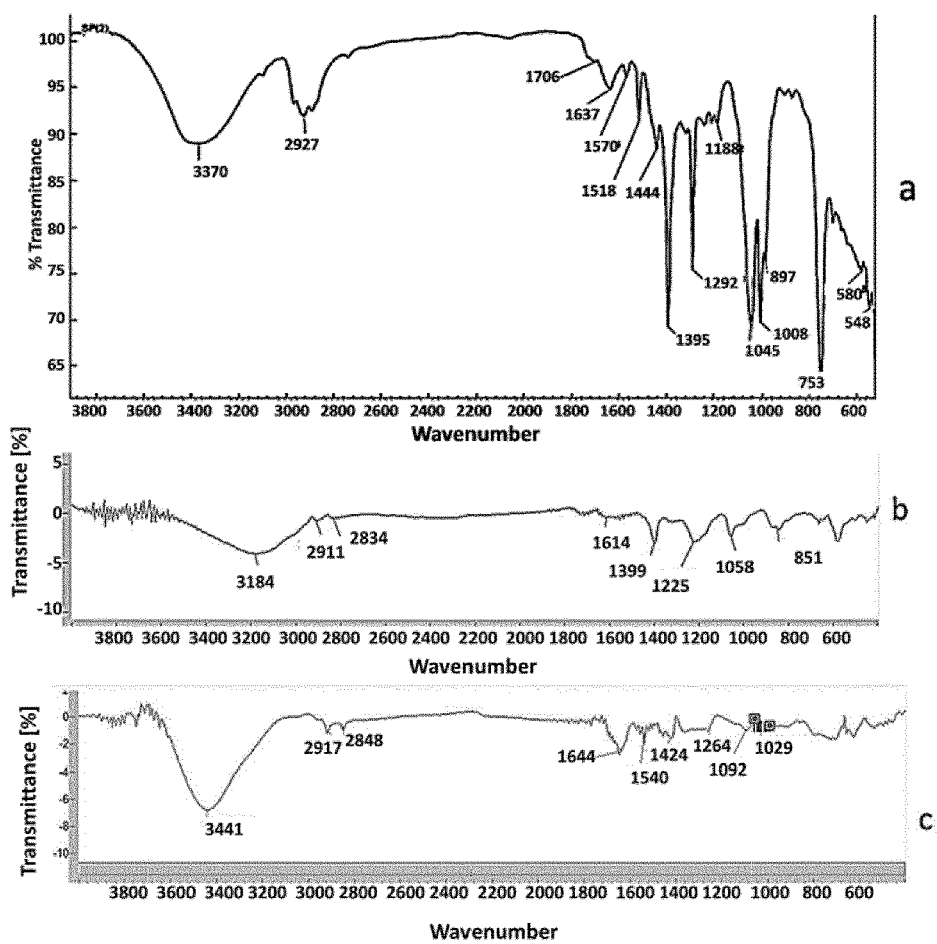
FIG. 8 shows the IR spectrum of the composition according to Example 5.

The sample of washed carbon black sample whose wash waters showed no absorption was analyzed by infrared (IR) spectroscopy. FIG. 8 shows the SP spectrum (FIG. 8 letter a) of the starting carbon black (FIG. 8 letter b), of the carbon after reaction and washing (FIG. 8 letter c). The IR spectrum in FIG. 8-c shows the characteristic peaks of SP, confirming the formation of the stable Carbon black-SP adduct.

Figure 9:
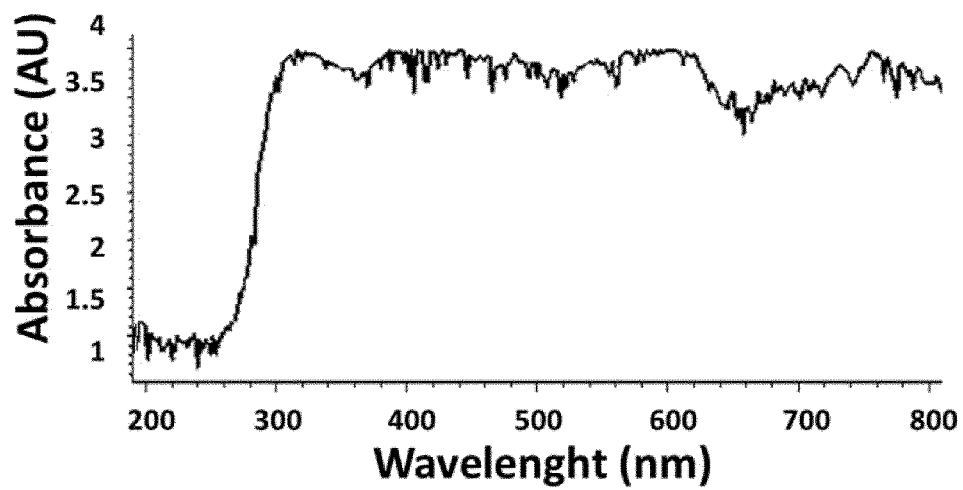
FIG. 9 shows the UV spectrum of the composition according to Example 5.

A suspension was also prepared with the sample of carbon black treated with SP after heating to 180° C. for 2 hours and after washing. The suspension, having a concentration of 1 mg/mL, was sonicated for 10 minutes and analyzed by ultraviolet (UV) spectroscopy. UV spectra were recorded immediately after sonication and after 24 hours and showed the same absorbance. FIG. 9 shows the spectrum recorded after 24 hours.

Figure 10:
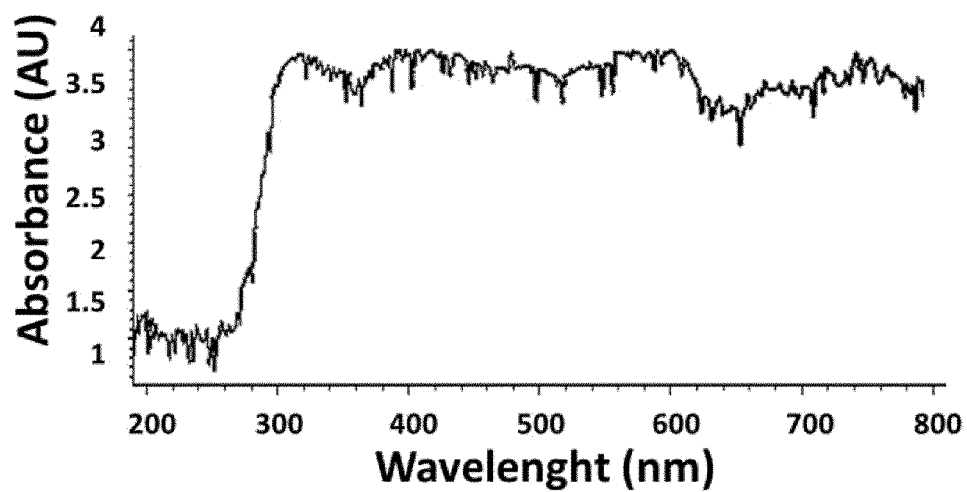
FIG. 10 shows the UV spectrum of the composition according to Example 5.

The suspension was then centrifuged at 2000 rpm, for 5 and for 30 minutes, without observing any reduction of absorbance in the UV absorption spectrum as shown in FIG. 10.

Example 6

Adduct of SP with nano-graphite.

The graphite used was Synthetic Graphite 8427, purchased from Asbury Graphite Mills Inc., with a minimum carbon content of 99.8% by weight and surface area of 330m²/g.

10 g of graphite and 100 mL of acetone were placed in a 250 mL one-neck round-bottom flask. The suspension was sonicated by ultrasonic bath for 15 minutes. After this time, a solution of 2.33 g of SP in 20 mL of acetone was added. The resulting suspension was sonicated for a further 15 minutes. The solvent was removed at reduced pressure. A powder consisting of graphite with adsorbed SP (graphite/SP adduct) was obtained.

0.300 g of graphite/SP adduct was placed in a 30 mL vial equipped with magnetic stirrer. The reaction mixture was heated to the temperature of 180° C. for 2 hours. After this time the powder was cooled to 25° C. The powder was then placed in a Buchner funnel with filter and washed repeatedly with distilled water. The filtrate was colorless. The wash water was analyzed by UV spectroscopy.

The samples of adduct collected after the thermal treatment times indicated and washed as illustrated were characterized by FT-IR analysis performed preparing a pellet of the adduct sample in KBr.

The sample of adduct heated to 180° C. for 2 hours was washed according to the procedure indicated and the wash waters were analyzed by UV spectroscopy. The UV spectrum showed no absorption.

Figure 11:
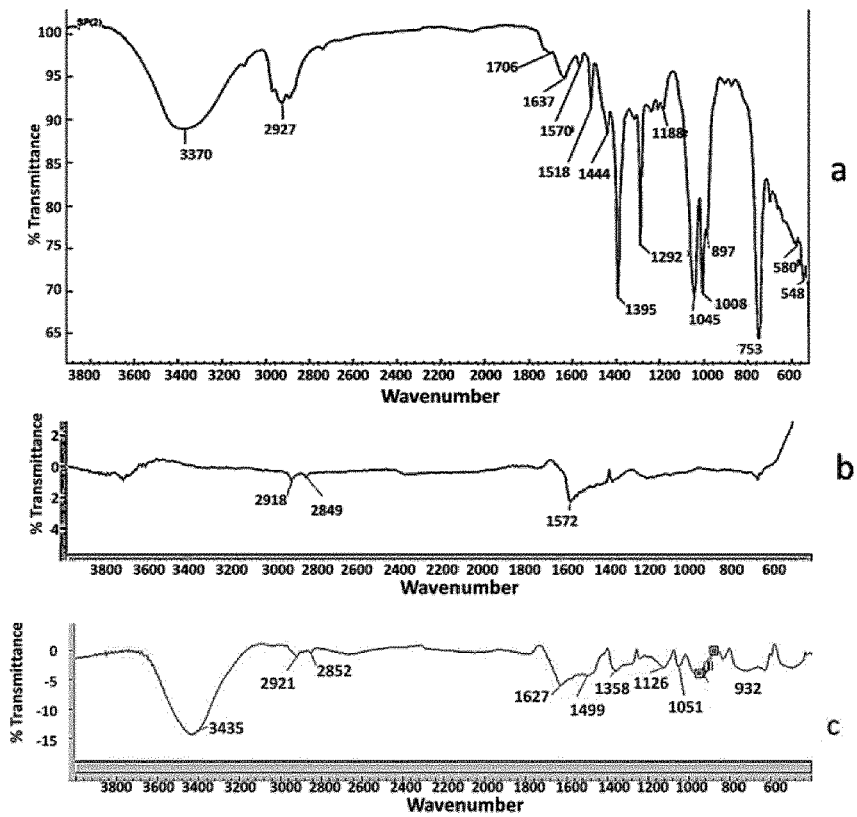
FIG. 11 shows the IR spectrum of the composition according to Example 6.

The washed nanoG sample whose wash waters showed no absorption were analyzed by infrared (IR) spectroscopy. FIG. 11 shows the SP spectrum (FIG. 11 letter a) of the starting nanoG (FIG. 11 letter b), of nanoG after reaction and washing (FIG. 11 letter c). The IR spectrum in FIG. 11-c shows the characteristic peaks of SP, confirming formation of the stable nanoG-SP adduct.

Figure 12:
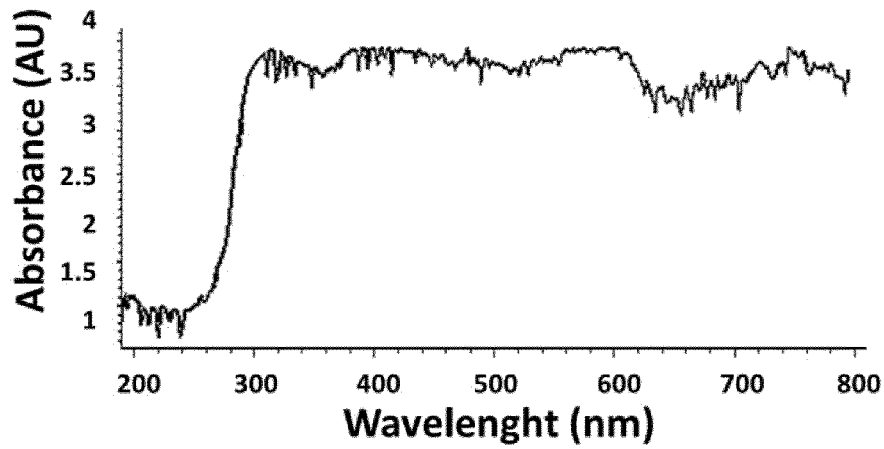
FIG. 12 shows the UV spectrum of the composition according to Example 6.

A suspension was also prepared with the sample of nanoG treated with SP after heating to 180° C. for 2 hours and after washing. The suspension, having a concentration of 1 mg/mL, was sonicated for 10 minutes and analyzed by ultraviolet (UV) spectroscopy. UV spectra were recorded immediately after sonication and after 24 hours and showed the same absorbance. FIG. 12 shows the spectrum recorded after 24 hours The suspension was centrifuged at 2000 rpm, for 5 and for 30 minutes. After centrifugation for 30 minutes, UV analysis showed no reduced absorbance with respect to the absorbance measured at t =0, without centrifugation.

Example 7

Adduct of SP with MWCNT.

The multiwall carbon nanotubes (MWCNT) used in this example were prepared according to the procedure indicated in EP2213369A1.

1 g of CNT was dispersed in 150 mL of ethyl acetate. The resulting suspension was sonicated for 30 minutes. 15 mL of a solution of ethyl acetate containing 117.5 mg of SP was added to the suspension. The resulting suspension was sonicated again for 30 minutes, and then the solvent was evaporated with a rotary evaporator, obtaining a grainy solid residue that was mechanically broken up and sieved to obtain a flowing powder consisting of SP adsorbed on CNT. The powder was spread on a flat glass plate, so as to form a thin layer of material, and was irradiated at 254 nm for 3 hours. Every 30 minutes, the material was remixed and spread on the glass plate again. 2 mg of the powder thus obtained was placed in $H_2O$ (2 mL) and sonicated for 30 minutes.

An aqueous suspension was prepared with the sample of CNT/SP treated for 3 hours with UV exposure. The suspension, having a concentration of 1 mg/mL, was sonicated for 10 minutes and analyzed by UV spectroscopy. UV spectra were recorded immediately after sonication and after 7 days and showed the same absorbance.

Example 8

Adduct of SP with MWCNT.

The multiwall carbon nanotubes (MWCNT) used in this example were prepared according to the procedure indicated in EP2213369A1.

2 g of CNT were dispersed in 150 mL of ethyle acetate. The resulting suspension was sonicated for 30 minutes. 5 mL of a solution of ethyl acetate containing 43 mg of SP was added to the suspension. The resulting suspension was sonicated again for 30 minutes, and then the solvent was evaporated with a rotary evaporator, obtaining a grainy solid residue that was mechanically broken up and sieved to obtain a flowing powder consisting of SP adsorbed on CNT. The powder was transferred to a quartz tube and maintained in suspension by a controlled air flow introduced from the top of the tube. The tube was irradiated at 254 nm for 1 hour.

An aqueous suspension was prepared with the sample of CNT/SP treated for 1 hour with UV exposure. The suspension, having a concentration of 1 mg/mL, was sonicated for 10 minutes and analyzed by UV spectroscopy. UV spectra were recorded immediately after sonication and after 7 days and showed the same absorbance.

Example 9

Adduct of SP with graphite.

The graphite used is Synthetic Graphite 8427, purchased from Asbury Graphite Mills Inc., with a minimum carbon content of 99.8% by weight and a surface area of 330 $m^2/g$. A suspension of 0.100 g of NanoG in 5 mL of dimethylformamide was sonicated for 30 minutes. 2 mL of a solution of 0.100 g of SP in dimethylformamide was added to this suspension. The resulting suspension was sonicated again for 30 minutes and the solvent was then removed with the rotary evaporator obtaining a flowing powder consisting of SP adsorbed on NanoG (graphite/SP adduct). The powder was placed in a quartz vial, so as to form a thin layer on one of the walls of the vial. The horizontally placed vial was irradiated at 254 nm for 3 hours, during which the vial was rotated every 30 minutes.

An aqueous suspension was prepared with the sample of NanoG treated with SP treated for 3 hours with UV exposure. The suspension, having a concentration of 1 mg/mL, was sonicated for 30 minutes and analyzed by UV spectroscopy. UV spectra were recorded immediately after sonication and after 1 hour and showed the same absorbance.

Some examples regarding the electrical conductivity properties of the adducts according to the present invention are illustrated below.

Example 10

Nano-graphite/SP adduct based coating on glass.

Deionized water in a ratio of 100 mg/mL was added to the nano-graphite/SP adduct prepared according to Example 2. The mixture obtained was mixed with a spatula. A coating layer on glass was then prepared by spreading a 2 mL front of the mixture with a bar (Printcoat Instruments) suitable to deposit a layer with a thickness of 40 microns. The coating layer was black, shiny and homogeneous in appearance. The water was removed from the coating layer in an oven for 1 hour. After this treatment, the coating layer was homogeneous and dark grey in appearance. The direct current (DC) electrical conductivity was measured using the four point probe method [L. J. Swartzendruber, Solid State Electron. 1964, 7, 413], using an FPP manual device (Jandel Engineering Ltd., UK) with a probe containing tungsten carbide needles (tip radius of 300 millimeters, needle spacing of 635 millimeters, load 60 g) coupled with a Keithley 2601 electrometer. Data were acquired and analyzed by CSM/Win Semiconductor Analysis Program software (MDC, US), and a resistivity of 2630 Ohm was detected.

Example 11

Nano-graphite/SP adduct based coating on paper.

Deionized water in a ratio of 100 mg/mL was added to the nano-graphite/SP adduct prepared according to Example 2. The mixture obtained was mixed with a spatula. A coating layer on paper was then prepared by spreading a 2 mL front of the mixture with a bar (Printcoat Instruments) suitable to deposit a layer with a thickness of 40 microns. The coating layer was black and homogeneous in appearance. The paper with the deposited layer was left at atmospheric temperature and pressure for 24 hours. After evaporation of the aqueous phase, the coating layer was homogeneous and black/dark grey in appearance. The direct current (DC) electrical conductivity was measured using the four point probe method [L. J. Swartzendruber, Solid. State Electron. 1964, 7, 413], using an FPP manual device (Jandel Engineering Ltd., UK) with a probe containing tungsten carbide needles (tip radius of 300 millimeters, needle spacing of 635 millimeters, load 60 g) coupled with a Keithley 2601 electrometer. Data were acquired and analyzed by CSM/Win Semiconductor Analysis Program software (MDC, US). A resistivity of 3550 Ohm was detected.

Example 12 (Comparison)

Nano-graphite based coating on paper.

The graphite used was Synthetic Graphite 8427, purchased from Asbury Graphite Mills Inc., with a minimum carbon content of 99.8% by weight and a surface areas of 330 $m^2/g$. Deionized water in a ratio of 100 mg/mL was added to the nanoG. The mixture obtained was mixed with a spatula. An attempt was made to spread a coating layer on paper, with a 2 mL front of the mixture with a bar (Printcoat Instruments) suitable to deposit a layer with a thickness of 40 microns. However, it was not possible to deposit a continuous layer, as most of the nanoG remained attached to the bar. Nonetheless, the direct current (DC) electrical conductivity was measured using the four point probe method [L. J. Swartzendruber, Solid State Electron. 1964, 7, 413], using an FPP manual device (Jandel Engineering Ltd., UK) with a probe containing tungsten carbide needles (tip radius of 300 millimeters, needle spacing of 635 millimeters, load 60 g) coupled with a Keithley 2601 electrometer. Data were acquired and analyzed by CSM/Win Semiconductor Analysis Program software (MDC, US). A resistivity of 4,320,000 Ohm was detected.

Example 13 (Comparison)

Nano-graphite/sodium dodecyl sulfate (SDS) adduct based coating on paper.

The graphite used was Synthetic Graphite 8427, purchased from Asbury Graphite Mills Inc., with a minimum carbon content of 99.8% by weight and a surface areas of 330 $m^2/g$. 200 mg of NanoG and 200 mg of SDS were mixed. Deionized water in a ratio of 100 mg/mL was added to the NanoG/SDS mixture. The mixture obtained was mixed with a spatula. A coating layer on paper was then prepared by spreading a 2 mL front of the mixture with a bar (Printcoat Instruments) suitable to deposit a layer with a thickness of 40 microns. The coating layer was black and homogeneous in appearance. The paper with the deposited layer was left at atmospheric temperature and pressure for 24 hours. The direct current (DC) electrical conductivity was measured using the four point probe method [L. J. Swartzendruber, Solid State Electron. 1964, 7, 413], using an FPP manual device (Jandel Engineering Ltd., UK) with a probe containing tungsten carbide needles (tip radius of 300 millimeters, needle spacing of 635 millimeters, load 60 g) coupled with a Keithley 2601 electrometer. Data were acquired and analyzed by CSM/Win Semiconductor Analysis Program software (MDC, US). A resistivity of 20000 Ohm, indicating poor conductivity, was detected. As can be deduced from the aforesaid example, it is possible to obtain a continuous and homogeneous coating layer of black fillers also by mixing them with normal surfactants; however this coating layer has poor electrical conductivity, which greatly limits its use.

Some examples regarding the dispersibility properties of the adducts according to the present invention and the related energy dissipation properties of the black fillers in the materials in which they are dispersed are illustrated below.

Example 14

Dispersion of nanographite reacted with SP in natural rubber latex.

Figure 13:
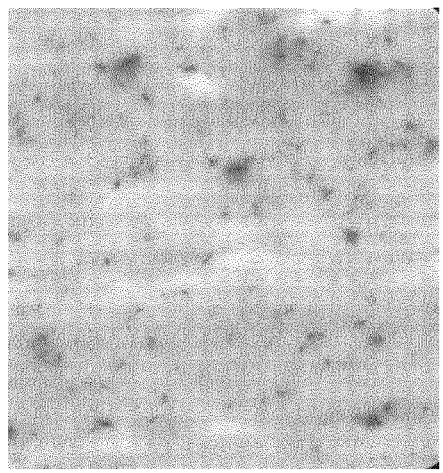
FIG. 13 shows an electron microscope photograph of the dispersion according to Example 14.
Figure 14:
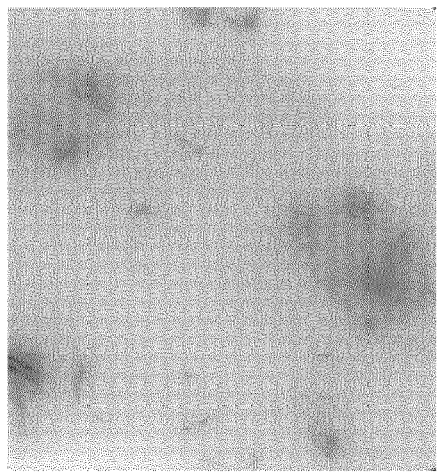
FIG. 14 shows an electron microscope photograph of the dispersion according to Example 14.

The natural rubber used was poly(1,4-cis-isoprene) from *hevea brasiliensis*, STR 20 produced by Thai Eastern Group. 0.05 grams of nanographite/SP adduct prepared according to Example 2 was added to 10 mL of water. The dispersion was then sonicated in a 2 liter ultrasonic bath with a power of 260 Watts for 15 minutes. A solution was obtained, in which no presence of powders was noted. This solution was added to 0.84 grams of latex. The dispersion obtained was stirred with magnetic stirrer for 60 minutes and then sonicated for 1 minute. Precipitation was then performed by adding a 0.1 M sulfuric acid solution. A composite material based on natural rubber containing nanographite was obtained. Transmission electron microscope analysis showed an extremely homogeneous dispersion of the carbon nanofiller as shown in FIGS. 13 and 14.

Example 15

Dispersion of Carbon Black reacted with SP in natural rubber latex.

The natural rubber used was poly(1,4-cis-isoprene) from *hevea brasiliensis*, STR 20 produced by Thai Eastern Group. 0.05 grams of Carbon black/SP adduct prepared according to Example 4 was added to 10 mL of water. The dispersion was then sonicated in a 2 liter ultrasonic bath with a power of 260 Watts for 15 minutes. A solution was obtained, in which no presence of powders was noted. This solution was added to 0.84 grams of latex. The dispersion obtained was stirred with magnetic stirrer for 60 minutes and then sonicated for 1 minute. Precipitation was then performed by adding a 0.1 M sulfuric acid solution. A homogeneous and continuous composite material based on natural rubber containing Carbon black was obtained.

Example 16 (Comparison)

Elastomeric compound with carbon black as reinforcing filler.

29.39 g of poly(1,4-cis-isoprene), commercial grade SKI 3 (by Nizhnekamskneftechim Export), was fed into a Brabender® internal mixer with a mixing chamber with a volume of 50 cc and masticated at 80° C. for 1 minute. 10.29 g of carbon black CB N326 (by Cabot) was then added, mixed for a further 5 minutes and the compound obtained was unloaded at 145° C. The composite thus prepared was then fed into the internal mixer at 80° C., adding 1.47 g of ZnO (by Zincol Ossidi) and 0.59 g of stearic acid (by Aldrich), and mixed for 2 minutes. 0.66 g of sulfur (by Solfotecnica) and 0.21 g of N-tert-butyl-2-benzothiazole sulfenamide (TBBS) (by Flexsys) were then added, mixing for a further 2 minutes. The composite was unloaded at 90° C.

Example 17 (Comparison)

Elastomeric compound with carbon black as reinforcing filler, in the presence of silane.

The compound was prepared according to the preparation of Example 16. 1.10 g of Bis[3-(triethoxysilyl)propyl]tetrasulfide silane (TESPT) was also added to the compound together with the carbon black.

Example 18

Elastomeric compound with carbon black treated with SP as reinforcing filler, in the presence of silane.

The compound was prepared according to the preparation of Example 16, the carbon black used for the preparation was pretreated with SP (10.89 g) according to the procedure of Example 4.

Dynamic Mechanical Characterization of the Compounds of Example 16, Example 17 and Example 18.

The compounds of Examples 16, 17 and 18 were vulcanized at 151° C. for 30 minutes. The value of the dynamic shear modulus was then measured, administering a sinusoidal strain at 50° C. and 1 Hz of frequency, in a strain amplitude ranging from 0.1% to 25%, using a Monsanto RPA 2000 rheometer.

Figure 15:
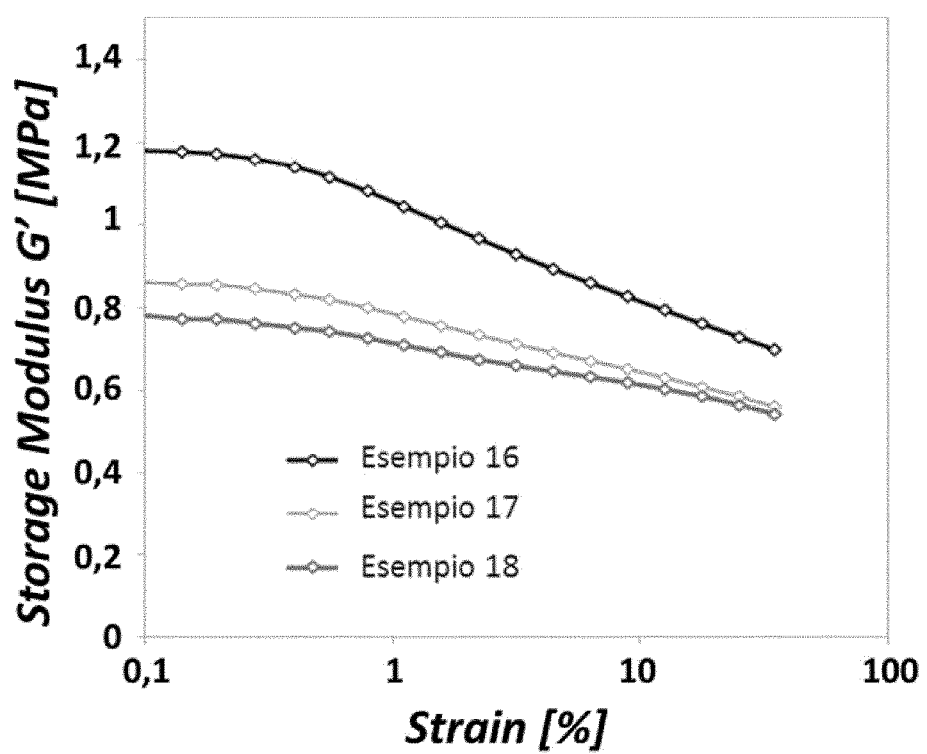
FIG. 15 shows the dependence of the dynamic modulus G' on the strain amplitude of the composition according to Examples 16, 17, 18.

Operating conditions: The samples were kept in the instrument at 50° C. for 90 seconds, the strain was then administered at 50° C. in the strain amplitude ranging from 0.1% to 25%, with frequency of 1 Hz, increasing the strain amplitude in the range indicated above. This treatment was implemented to cancel the prior thermomechanical history. Administration of strain was then repeated with the same experimental conditions. Vulcanization was then carried out at 150° C. for 30 minutes, with a frequency of 1.667 Hz and an angle of 6.98% (0.5 rad). The vulcanized sample was left in the instrument for 10 minutes at 50° C. The sinusoidal strain was then applied with the same conditions indicated above, leaving the sample in the instrument for 10 minutes at 50° C. The sinusoidal strain was then applied once again, with the same experimental conditions. FIG. 15 shows the strain amplitude dependence of the dynamic modulus G'. It can be observed how the composite prepared in Example 18 shows a lower modulus value at minimum strain and shows a smaller decrease of the modulus with the increase in strain amplitude. Reduction of dynamic modulus with the strain amplitude is a phenomenon known as the Payne effect and is correlated with energy dissipation of the composite material or of the black fillers.

The invention claimed is:

1. An adduct of a compound of formula (I)

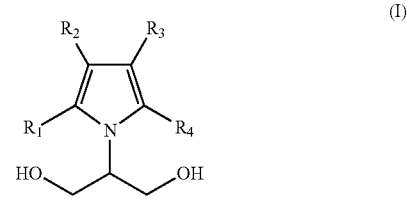

wherein $R_1$, $R_2$, $R_3$, $R_4$ are independently selected from the group consisting of: hydrogen, $C_1$-$C_3$ alkyl, $C_2$-$C_{22}$ linear or branched alkenyl or alkynyl, aryl, $C_1$-$C_{22}$ linear or branched alkyl-aryl, $C_2$-$C_{22}$ linear or branched alkenyl-aryl, and $C_2$-$C_{22}$ linear or branched alkynyl-aryl, heteroaryl; and a carbon allotrope or a carbon allotrope derivative, wherein the carbon is $sp^2$ hybridized and wherein said carbon allotrope derivative is an $sp^2$ hybridized carbon allotrope with at least one functional group selected from the group consisting of: oxygenated functional groups, functional groups containing carbonyls, functional groups containing nitrogen atoms, and functional groups containing sulfur atoms, wherein the oxygenated functional groups are hydroxyls or epoxies; wherein the functional groups containing carbonyls are aldehydes, ketones or carboxylic acids; wherein the functional groups containing nitrogen atoms are amines, amides, nitriles, diazonium salts, or imines; and wherein the functional groups containing sulfur atoms are sulfides, disulfides, mercaptans, sulfones, or sulfonic groups.

2. The adduct according to claim 1, wherein $R_1$, $R_2$, $R_3$ and $R_4$ are independently selected from the group consisting of: H, $CH_3$, $CH_2CH_3$, and phenyl.

3. The adduct according to claim 1, wherein said carbon allotrope or it's derivative are selected from the group consisting of: carbon black, fullerene, single-wall or multi-wall carbon nanotubes, graphene, and graphite with a number of graphene layers from 2 to 10000.

4. The adduct according to claim 1, wherein said carbon allotrope derivative is graphite oxide.

5. The adduct according to claim 1, wherein said carbon allotrope derivative is graphene oxide.

6. A process for the preparation of an adduct comprising a compound of formula (I)

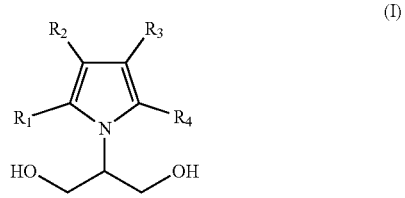

(I)

wherein $R_1$, $R_2$, $R_3$, $R_4$ are independently selected from the group consisting of: hydrogen, $C_1$-$C_3$ alkyl, $C_2$-$C_{22}$ linear or branched alkenyl or alkynyl, aryl, $C_1$-$C_{22}$ linear or branched alkyl-aryl, $C_2$-$C_{22}$ linear or branched alkenyl-aryl, and $C_2$-$C_{22}$ linear or branched alkynyl-aryl, heteroaryl; and a carbon allotrope or a carbon allotrope derivative, wherein the carbon is $sp^2$ hybridized and wherein said carbon allotrope derivative is an $sp^2$ hybridized carbon allotrope with at least one functional group selected from the group consisting of: oxygenated functional groups, functional groups containing carbonyls, functional groups containing nitrogen atoms, and functional groups containing sulfur atoms;

wherein the oxygenated functional groups are hydroxyls or epoxies;

wherein the functional groups containing carbonyls are aldehydes, ketones or carboxylic acids; wherein the functional groups containing nitrogen atoms are amines, amides, nitriles, diazonium salts, or imines; and wherein the functional groups containing sulfur atoms are sulfides, disulfides, mercaptans, sulfones, or sulfonic groups; and wherein the process comprises:
  i. providing a solution of a compound of formula (I) in a protic or aprotic polar solvent;
  ii. providing a suspension of the carbon allotrope in the protic or aprotic polar solvent used for the preparation of the solution in i.;
  iii. mixing said solution and said suspension;
  iv. removing said solvent from said mixture obtained in iii.; and
  v. providing thermal and/or mechanical energy and/or photon irradiation energy to the mixture obtained in iv.

7. The process according to claim 6, wherein said thermal energy is provided at a temperature from 50 to 180° C. for from 15 to 360 minutes.

8. The process according to claim 6, wherein said mechanical energy is provided from 15 to 360 minutes.

9. The process according to claim 6, wherein said photon irradiation energy is provided at a wavelength from 200 to 380 nm for 30 to 180 minutes.

* * * * *